(12) United States Patent
Wu et al.

(10) Patent No.: US 7,205,333 B2
(45) Date of Patent: Apr. 17, 2007

(54) MULTIVALENT NEURAMINIDASE INHIBITOR CONJUGATES

(76) Inventors: Wen-Yang Wu, 34 Munro Avenue, Mount Waverly, Victoria 3149 (AU); Michael Dennis Dowle, C/-GlaxoSmith Kline, Gunnels Wood Road, Stevenage, Hartfordshire (GB) SG1 2NY; Betty Jin, 34 Munro Avenue, Mount Waverley, Victoria 3149 (AU); Simon John Fawcett Macdonald, C/-GlaxoSmith Kline, Gunnels Wood Road, Stevenage, Hartfordshire (GB) SG1 2NY; Andrew McMurtrie Mason, C/-GlaxoSmith Kline, Gunnels Wood Road, Stevenage, Hartfordshire (GB) SG1 2NY; Darryl McConnell, Unterbergergasse 4/Top 32, Wien A - 1200 (AT); Keith Watson, 23 Erasmus Street, Surrey Hills, Victoria 3127 (AU)

( * ) Notice: Subject to any disclaimer, the term of this patent is extended or adjusted under 35 U.S.C. 154(b) by 15 days.

(21) Appl. No.: 10/363,988

(22) PCT Filed: Sep. 7, 2001

(86) PCT No.: PCT/AU01/01128

§ 371 (c)(1),
(2), (4) Date: Oct. 14, 2003

(87) PCT Pub. No.: WO02/20514

PCT Pub. Date: Mar. 14, 2002

(65) Prior Publication Data

US 2004/0058853 A1    Mar. 25, 2004

(30) Foreign Application Priority Data

Sep. 8, 2000    (AU) ................................. PR0010

(51) Int. Cl.
A61K 31/35    (2006.01)
C07D 307/02   (2006.01)

(52) U.S. Cl. ...................... 514/451; 514/557; 549/419; 549/420; 562/405

(58) Field of Classification Search ............... 549/419, 549/420; 562/405; 514/451, 557
See application file for complete search history.

(56) References Cited

U.S. PATENT DOCUMENTS 6,022,888 A * 2/2000 Morishige et al. .......... 514/455

FOREIGN PATENT DOCUMENTS

| | | |
|---|---|---|
| EP | 0 823 428 B1 | 2/1998 |
| WO | WO 91/16320 A1 | 10/1991 |
| WO | WO 95/18800 A1 | 7/1995 |
| WO | WO 95/20583 A1 | 8/1995 |
| WO | WO 95/34595 | 12/1995 |
| WO | WO 95/34595 A1 | 12/1995 |
| WO | WO 96/26933 A1 | 9/1996 |
| WO | WO 97/06157 A1 | 2/1997 |
| WO | WO 97/32214 | 9/1997 |
| WO | WO 97/47194 A1 | 12/1997 |
| WO | WO 98/03572 | 1/1998 |
| WO | WO 98/03572 A1 | 1/1998 |
| WO | WO 98/06712 A1 | 2/1998 |
| WO | WO 98/21243 | 5/1998 |
| WO | WO 98/21243 A1 | 5/1998 |
| WO | WO 99/33781 A1 | 7/1999 |
| WO | WO 00/55149 | 9/2000 |
| WO | WO 00/55149 A1 | 9/2000 |

OTHER PUBLICATIONS

Mathai Mammen et al., "Polyvalent Interactions in Biological Systems: Implications for Design and Use of Multivalent Ligands and Inhibitors", Angew. Chem. Int. Ed. 1998, 37, 2754-2794.

George B. Sigal et al., "Polyacrylamides Bearing Pendant α-Sialoside Groups Strongly Inhibit Agglutination of Erythrocytes by Influenza Virus: The Strong Inhibition Reflects Enhanced Binding through Cooperative Polyvalent Interactions", Journal of the American Chemical Society, vol. 118, No. 16, Apr. 24, 1996, pp. 3789-3800.

Mathai Mammen et al., "Effective Inhibitors of Hemagglutination by Influenza Virus Synthesized from Polymers Having Active Ester Groups, Insight into Mechanism of Inhibition", J. Med. Chem. 1995, 38, 4179-4190.

Jon D. Reuter et al., "Inhibition of Viral Adhesion and Infection by Sialic-Acid-Conjugated Dendritic Polymers", Bioconjugate Chem. 1999, 10, 271-278.

Frederick G. Hayden et al., "Efficacy and Safety of the Neuraminidase Inhibitor Zanamivir in the Treatment of Influenzavirus Infections", The New England Journal of Medicine, Sep. 25, 1997, pp. 874-880.

P. Meindl et al., "Inhibition of Neuraminidase Activity by Derivatives of 2-Deoxy-2, 3-dehydro-N-acetylneuraminic Acid", Virology 58, 457-463 (1974).

* cited by examiner

Primary Examiner—Golam M. M. Shameem
Assistant Examiner—Robert Shiao
(74) Attorney, Agent, or Firm—Foley & Lardner LLP

(57) ABSTRACT

The invention relates to a multimeric compound or a pharmaceutically acceptable salt or derivative thereof which comprises three or more neuraminidase-binding groups attached to a spacer or linking group, in which the neuraminidase-binding group is a compound which binds to the active site of influenza virus neuraminidase, but is not cleaved by the neuraminidase. The invention also relates to processes for the preparation of the multimeric compound defined above, pharmaceutical compositions containing them or methods for the treatment and/or prophylaxis of a viral infection involving them.

39 Claims, No Drawings

MULTIVALENT NEURAMINIDASE INHIBITOR CONJUGATES

This application is a 371 of PCT/AU01/01128 filed on Sep. 7, 2001.

This invention relates to a new class of chemical compounds and their use in medicine. In particular the invention provides novel multivalent neuraminidase inhibitor conjugates, processes for their preparation, pharmaceutical compositions thereof and their use as anti-influenza agents. The invention also provides a novel diagnostic method which can be used for detection of all types of influenza A and B virus.

BACKGROUND OF THE INVENTION

Enzymes with the ability to cleave N-acetyl neuraminic acid (NANA), also known as sialic acid, from other carbohydrates are present in many microorganisms. These include bacteria such as *Vibrio cholerae, Clostridiun perfringens, Streptococcus pneumoniae* and *Arthrobacter sialophilus*, and viruses such as influenza virus, parainfluenza virus, mumps virus, Newcastle disease virus and Sendai virus. Most of these viruses are of the orthomyxovirus or paramyxovirus groups, and carry a neuraminidase activity on the surface of the virus particles. Many of these neuraminidase-possessing organisms are major pathogens of man and/or animals, and some, such as influenza virus and Newcastle disease virus, cause diseases of enormous importance.

Influenza A and B viruses are major causes of acute respiratory disease, resulting in an estimated 30–50 million infections annually in the United States alone. Influenza A has been responsible for major epidemics, such as the "Spanish Flu" of 1919 which killed millions of people. Influenza remains a difficult disease to control, resulting in significant morbidity, and mortality largely due to secondary infection in eldery or debilitated patients. Vaccines are continually being rendered obsolete by antigenic shift or drift, and consequently immunization is only about 70% effective in preventing infection. Until recently, the only drugs approved by regulatory authorities for treatment of influenza were amantadine and rimantadine, which are ineffective against influenza B, and are known to have serious side-effects. In addition, rapid antiviral resistance to both of these compounds have been shown to be a frequent event with these compounds.

Influenza A and B have two major surface glycoproteins, haemagglutinin (HA) and the enzyme neuraminidase (NA), which are both essential for infectivity. It is believed that HA is necessary for the virus to attach to cells, whereas NA is needed for release of the virus from cell surfaces. There are typically about 600 trimeric HA and about 50 copies of the NA tetramer units on the surface of each virus particle. Both HA and NA therefore are attractive potential targets in the search for anti-influenza drugs.

Influenza virus haemagglutinin binds to the sialic acid-containing glycoproteins and glycolipids on cell-surface receptors, thereby initiating the process of attachment of the virus to a cell and subsequent infection. The strength of the binding of a virus particle to the cell membrane appears to depend on the interaction of multiple copies of the influenza HA with multiple sialic acid groups on the cell surface.

Using this concept of a polyvalent interaction (Mammen et al., Angew. Chem., 1998 37: 2754–2794), several workers have reported the synthesis of macromolecules containing two or more sialic acid derivatives which act as haemagglutinin inhibitors. Although some strong HA inhibitors have been discovered, none of these polyvalent macromolecules has been shown to prevent influenza infection in vivo. Recent papers by Whitesides and other workers (J. Amer. Chem. Soc., 1996 118 3789–3800; J. Medicinal Chem., 1995 38 4179–4190; Bioconjugate Chemistry, 1999 10: 271–278) have summarised the various attempts to use this approach to the design of inhibitors of influenza haemagglutinin.

It has long been thought that inhibitors of neuraminidase might prevent infection by neuraminidase-bearing viruses. Most of the known neuraminidase inhibitors are analogues of neuraminic acid, such as 2-deoxy-2,3-dehydro-N-acetylneuraminic acid (DANA) and some of its derivatives (Meindl et al, Virology, 1974 58 457). Our International Patent Publication No. WO 91/16320 describes a number of analogues of DANA which are active against viral neuraminidase, and it has been shown in particular that 4-guanidino-2-deoxy-2,3-dehydro-N-acetylneuraminic acid (Compound (A), code number GG167) is useful in the treatment of influenza A and B (N. Engl. J. Med., 1997 337 874–880). Other patent applications describe various closely-related sialic acid derivatives (eg. PCT Publications No. WO95/18800, No. WO 95/20583 and No. WO 98/06712), and anti-viral macromolecular conjugates of GG167 have also been described (International Patent Application No. PCT/AU97/00771, WO98/21243).

Compound (A)

(Relenza™)

Ac represents acetyl

In addition to the sialic acid-based inhibitors mentioned above, other types of highly active inhibitors of influenza virus neuraminidase have also been described, particularly those based on 5- and 6-membered carbocyclic ring systems (eg. International Patent Publications No. WO96/26933 and No. WO97/47194). Despite intense research activity, to date only two anti-influenza drugs which act at the NA site, "Relenza" (Trade mark of Glaxo Wellcome plc) and "Tamiflu" (Trade mark of Hoffman-LaRoche AG) have been approved for clinical use. Other neuraminidase inhibitors have been disclosed in WO99/33781, specifically (1S,2S, 3R,4R)-3-[(1R)-1-(acetylamino)-2-ethylbutyl]-4-{[amino (imino)methyl]amino]-2hydroxycyclopentane carboxylic acid, which is in phase III clinical trials.

Recently, International Patent Publication No. WO97/06157, No. WO98/06712 and European Patent Application No. 0823428 have described certain derivatives of compound (A) in which the normal sialic acid 7-hydroxy group is replaced by various other functionalities, which inhibit multiplication of the influenza virus.

International Patent Publication Nos. WO95/34595 and WO98/03572, by Biomolecular Research Institute Ltd, respectively disclose dendrimers having a plurality of terminal groups and linear polymers having a plurality of side chain groups. In WO95/34595, the terminal groups may inter alia be anionic, and may contain a carboxylic acid group. Sialic acid and related compounds are neither disclosed nor suggested. In WO98/03572, the side chain groups may be sialic acid or a derivative thereof; the only example of such a compound utilises linkage of the sialic acid moiety via a sulphur atom at the 2-position, in line with the conventional wisdom at that time. The use of 2,3-dehydrosialic acid derivatives as side chain groups is neither disclosed nor suggested.

In our International patent application No. PCT/AU00/00165 filed on Mar. 9, 2000, we showed that when two neuraminidase-binding compounds are suitably linked together through a region of the molecule that is not involved in binding to the active site, the resultant dimers show enhanced anti-viral activity. In particular we have found that, although an extra substituent attached to compound (A) at the 7-position generally causes a slight decrease in the anti-influenza potency, when two such 7-substituted molecules of compound (A) are both attached to a suitable spacer moiety, the anti-influenza activity can be significantly improved. Though not wishing to be bound or limited by any proposed mechanism for the observed effect, we believe that the dimeric compounds have improved anti-influenza activity because they may be able to bind to two separate neuraminidase molecules, and thereby cause aggregation of the neuraminidase tetramers and/or the influenza virions, or that by having one copy of zanamivir bound to the active site of the neuraminidase, and a second copy in close proximity, then the binding kinetics may be more efficient, in that as one copy dissociates the second copy can bind more rapidly than a free molecule of zanamivir. We have now shown that multivalent neuraminidase inhibitor conjugates, ranging up to dendrimer-type molecules, have longer duration of action. Again without wishing to be bound by theory, the basis for the long residency time in the lungs is thought to be due to the size and molecular weight of the macromolecule preventing entry through tight junctions in the respiratory epithelium, and the polarity of the macromolecule being such that passage through the cell membranes occurs very inefficiently. An alternative theory is that the compounds themselves interact with the phospholipids in the cell membrane or other components of the respiratory epithelium, and increase the residency time in the lungs.

It will be clearly understood that, although a number of prior art publications are referred to herein, this reference does not constitute an admission that any of these documents forms part of the common general knowledge in the art, in Australia or in any other country.

SUMMARY OF THE INVENTION

In a first aspect, the invention provides a discrete multimeric compound which comprises three or more neuraminidase-binding groups attached to a spacer or linking group, in which the neuraminidase-binding group is a compound which binds to the active site of influenza virus neuraminidase, provided that it is not cleaved by the neuraminidase.

The neuraminidase-binding group should advantageously itself have a high binding affinity; preferably the Kd or $IC_{50}$ for the NA-binding group will be of $10^{-6}$M or better. The covalent attachment of a linking group on to a single neuraminidase inhibitor may cause some reduction in the ability to bind to the enzyme relative to the parent molecule (eg. Compound A), but when several such ligands are attached to a common backbone there may be an increase in the average binding through the effects of multivalency.

Preferably the multivalent molecule comprises three or more neuraminidase-binding neuraminic acid (sialic acid) derivatives or cyclopentyl or cyclohexenyl carboxylic acid derivatives covalently attached to a common backbone group comprising a core or both a core and a spacer. The compounds of the invention are discrete molecular entities which are made up of at least 80%, and preferably 90% of a common molecular structure with a definable, measurable purity and a specific molecular weight (MW). Thus the compounds of the invention are more amenable to development as pharmaceutical agents than the polydisperse macromolecular conjugates of our earlier application PCT/AU97/00771, which are comprised of mixtures of polymer chains of varying MW and substitution pattern.

In a preferred embodiment, the invention provides a compound of formula (I):

in which:

X is O or $CH_2$;

R is an azido group, a hydroxy group, an optionally substituted guanidino group, an optionally substituted amino group, an optionally substituted amidine, or an optionally or substituted imidate;

$R^2$ is $COCR^3_3$ or $SO_2CR^3_3$;

$R^3$ is independently selected from H, F, Cl, Br, I and $C_{1-6}$alkyl;

n is an integer of from 2 to 128;

Y is —O, —O(C=O), —$NR^4$, —$NR^4CO$, —O(C=O)$NR^4$, —O(C=S)$NR^4$, —$NR^4$(C=O)O, —$NR^4$(C=S)O, —$NR^4$(C=O)$NR^4$, —$NR^4$(C=S)$NR^4$, —$NR^4SO$, —$NR^4SO_2$, —$NR^4SONR^4$, or —$NR^4SO_2NR^4$ in which $R^4$ is H or $C_{1-6}$alkyl;

CG is a core group selected from an optionally substituted cyclic, straight or branched group or a combination thereof having from 1 to 200 atoms in its backbone, in which the backbone atoms are selected from C, N, O and S; and L is a linking group of from 0 to 20 backbone atoms, in which the backbone and terminal atoms are selected from C, N, O and S;

or a pharmaceutically acceptable derivative thereof and/or an isomer thereof. Preferably X is O.

Preferably R is an optionally substituted amino or guanidino group, more preferably an unsubstituted amino or guanidino group.

Preferably $R^3$ is H, F or $C_{1-6}$alkyl.

Preferably n is an integer from 2 to 7, more preferably, n is 2 or 3.

Preferably Y is —O or —O(C=O)NR$^4$, more preferably —O(C=O)NR$^4$ in which R$^4$ is H and the group is bonded to the linking group L through the N atom.

Preferably the linking group L is of from 1 to 15 backbone atoms.

More preferably the linking group L is —HN(CH$_2$)$_p$, in which p is an integer from 2 to 10, more preferably p is 6 and wherein the linking group L is bonded to the core group (CG) through the N atom.

The atom which the linking group L binds to Y is referred to as the terminal atom.

In one embodiment, the compound of the invention is a dendrimer, which carries terminal groups which are neuraminidase-binding groups. Suitable dendrimer carriers and their preparation are well known, as described in International patent applications no. WO95/24221 and WO95/34595, and U.S. Pat. Nos. 4,289,872, 4,410,688, 4,507,466, 4,558,120, 4,568,737 and 4,587,329. Polyamidoamine (PAMAM) dendrimers are particularly preferred, and PAMAM dendrimers with 0.8 to 128 end groups are commercially available. PAMAM dendrimers based on either an ammonia core or on an ethylene diamine core may be used. Alternatively, asymmetrical polylysine dendrimers based on a benzhydrylamine core with lysine branching units may also be used. Such dendrimers are described in U.S. Pat. No. 4,289,872 and U.S. Pat. No. 4,410,688. Other suitable dendrimer types are described in the recent chemical literature (see for example Angew. Chemie, 1999 38 884; Bioconjugate Chemistry, 1999 10 1115). The person skilled in the art will readily be able to determine which dendrimer type is most suitable for a specific purpose.

In a particularly preferred embodiment the invention provides compounds of formula (I) which are trimeric, tetrameric, pentameric, hexameric, heptameric, or octameric compounds. Preferably the compounds are conjugates of 7-carbamate derivatives of compound A (GG167), ie. R=guanidine, R$^2$ is acetyl, X is oxygen, Y is O(C=O)NH and n is chosen from one of the integers 2, 3, 4, 5, 6 and 7.

The molecular weight of the compounds of the invention is generally in the range of from about 1,000 to about 100,000, and preferably from about 1,000 to about 10,000, even more preferably about 1,000 to about 5,000. The person skilled in the art will readily be able to optimize the length and structure of the linking groups by routine experimentation.

The biological activity of the compounds of the invention is based on the use of ligands on the backbone which are able to bind specifically to the active site of influenza virus neuraminidase, or of functionalised derivatives of such compounds. The term "neuraminidase binders" is used herein to refer to these compounds and their functionalized derivatives. The preferred neuramindase binding group is based on a compound of formula (A). The method and compounds of the invention can function either in the presence or the absence of compounds binding non-specifically to influenza virus neuraminidase. The neuraminidase binder may be any agent which binds to the active site of influenza virus neuraminidase, provided that it is not cleaved by the enzyme. The binding need not be irreversible, but the binding group should have a high binding affinity, preferably a Kd or IC$_{50}$ of 10$^{-6}$ M or better.

In general it is intended that when any variable occurs twice in formula (I), the variable may be the same or different.

Where R is a substituted amino or guanidino group, suitable substituents include, but are not limited to, C$_{1-6}$alkyl, hydroxyC$_{1-6}$alkyl, allyl, nitrile, C$_{1-6}$alkoxycarbonyl and C$_{1-6}$acyl.

Suitable core groups CG include, but are not limited to, optionally substituted straight or branched hydrocarbon chains, optionally containing heteroatoms selected from N, o or S, peptides, oligosaccharides, cyclodextrins, polyamidoamines, polyethylenimines, polyalkyl and polyaryl ethers, polyamidoalcohols, calixarenes, polyaminoacids, polyethylene glycol units, alkylamidoalkanes, oligolactates, oligoglycolates, ethylenediamine tetraacetic acid (EDTA), aryl, cycloalkyl, heterocyclic rings and heteroaryl groups wherein the heteroatoms are selected from N, S, and O. Any one of these groups may be may be used alone, in multiple form or in combination with any other. Dendrimer compounds are one type of core group. The core group CG may also optionally have attached to it an extra functionality to improve the pharmaceutical or pharmokinetic properties of the compound. Such functionalities include lipophilic hydrocarbon groups, polyethylene glycol (PEG) chains, peptides and ionic groups.

Preferred core groups include optionally substituted straight or branched hydrocarbon groups, optionally comprising heteroatoms selected from N, O and S, peptides, polyamidoamines, EDTA, polyethylene glycol units, calixarenes, aryl, cycloalkyl, heterocyclic and heteroaryl groups or a combination thereof.

More preferably the core group is selected from the following groups optionally substituted straight or branched hydrocarbon groups, optionally comprising heteroatoms selected from N, O and S, EDTA, aryl, cycloalkyl, heterocyclic and heteroaryl groups or a combination thereof.

In a particularly preferred embodiment of the invention the core group CG, the linking group L, and/or the group Y of the compound are selected to impart longer-lasting lung residence properties to the compounds of Formula (I). These properties may for example be improved through the inclusion of extra ionic groups on the core structure, or through using backbone molecules which impart increased viscosity to the final conjugates.

The term "hydrocarbon" refers to alkyl, alkenyl or alkynyl groups.

The term "aryl" refers to an unsaturated aromatic carbocyclic group of from 6 to 20 carbon atoms having a single ring (e.g. phenyl) or multiple condensed (fused) rings (e.g. naphthyl or anthryl). Preferred aryl groups are phenyl or naphthyl.

The term "polyaminoacid" refers to a group comprising more than one amino acid. Suitable amino acids typically are alpha amino acids, i.e. compounds characterised by one amino or imino nitrogen atom separated from the carbon atom of one carboxyl group by a single substituted or unsubstitued alpha carbon atom.

The term "alkyl" refers to a branched or unbranched saturated hydrocarbon chain, preferably having from 1 to 40 carbon atoms, preferably 1 to 10 carbon atoms, more preferably 1 to 6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated. Examples of cyclic alkyl groups include cyclo-hexyl and cyclobutyl.

"Alkenyl" refers to a branched or unbranched unsaturated hydrocarbon, preferably having from 2 to 40 carbon atoms, preferably 2 to 10 carbon atoms, more preferably 2 to 6 carbon atoms, and preferably having 1 to 6 double bonds. This term is further exemplified by such groups as vinyl, prop-2-enyl, pent-3-enyl, hex-5-enyl, 5-ethyldodec-3,6-dienyl, and the like.

"Alkynyl" refers to an unsaturated hydrocarbon, preferably having from 2 to 40 carbon atoms, preferably 2 to 10 carbon atoms, more preferably 2 to 6 carbon atoms, and preferably having 1 to 6 triple bonds. This term is further exemplified by groups such as acetylenyl, prop-2-ynyl, pent-3-ynyl, hex-5-ynyl, 5-ethyldodec-3,6-diynyl, and the like.

The term "heteroaryl" refers to an aromatic group of from 1 to 15 carbon atoms and 1 to 4 heteroatoms selected from oxygen, nitrogen and sulphur within at least one ring (if there is more than one ring). The term "heterocyclic" refers to a cyclic alkyl, alkenyl or alkynyl group of from 1 to 40 carbon atoms and 1 to 4 heteroatoms selected from oxygen, nitrogen and sulphur within at least one ring (if there is more than one ring). Examples of heterocyclic groups include piperazine and tetrahydrofuran.

Suitable substituents for all of the groups used as core or linking groups include Br, Cl, F, I, $CF_3$, $NH_2$, hydroxy, substituted amino groups such as NHacyl, $C_{1-6}$alkylamino, carboxy, sulphonic acid, sulphoxides, sulphonamides, quaternary ammonium groups and $C_{1-6}$alkoxy groups such as methoxy, and are preferably F, Cl, hydroxy, $C_{1-6}$alkoxy, amino, $C_{1-6}$alkylamino or carboxy.

Halide will be understood to mean Cl, F, Br or I.

The term "isomer" is used herein in its broadest sense and includes structural, geometric and stero isomers. As the compound of formula (I) may have one or more chiral centres, it is capable of existing in enantiomeric forms.

For the purposes of this specification it will be clearly understood that the word "comprising" means "including but not limited to", and that the word "comprises" has a corresponding meaning.

lp;.5pIt will be appreciated by those skilled in the art that the compounds of formula (I) may be modified to provide pharmaceutically acceptable derivatives thereof at any of the functional groups in the compounds of formula (I). Of particular interest as such derivatives are compounds modified at the carboxyl function, hydroxyl functions or at the guanidino or amino groups. Thus compounds of interest include $C_{1-6}$alkyl esters, such as methyl, ethyl, propyl or isopropyl esters, aryl esters, such as phenyl, benzoyl esters, and $C_{1-6}$acetyl esters of the compounds of formula (I).

A further preferred embodiment is represented by compounds of formula (II):

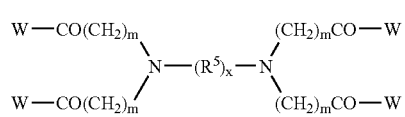

(II)

wherein

W can independently be OH, $N(R^4)_2$ or -L-Y—B, in which $R^4$ is as defined above;

x is an integer from 1 to 10;

m is an integer from 1 to 4, preferably 1 or 2;

$R^5$ is aryl, heteroaryl, cyclic $C_{1-10}$ alkyl, or heterocylic $C_{1-10}$ alkyl, or an optionally substituted $C_{1-10}$ alkyl, $C_{3-10}$ alkenyl or $C_{3-10}$alkynyl in which one or more of the C atoms in the chain can optionally be replaced by a heteroatom selected from N, O and S or a combination thereof;

L is as defined in compounds of formula (I);

Y is as defined for compounds of formula (I);

B is H or a compound of formula (B):

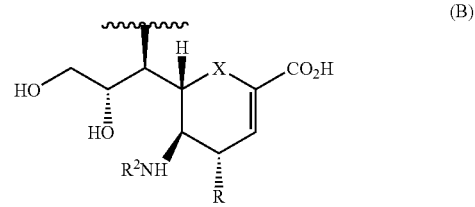

(B)

in which X, R and $R^2$ are as defined in compounds of formula (I);

with the provisos that:

B cannot be H when Y is —NH(C=O)O or —NH(C=S)O;

not more than one W can be OH or $N(R^3)_2$ and not more than one B can be H, and W cannot be OH $N(R^4)_2$ when B is H;

or pharmaceutically acceptable derivatives thereof.

Tetrameric compounds of the invention may be represented by the following general formula:

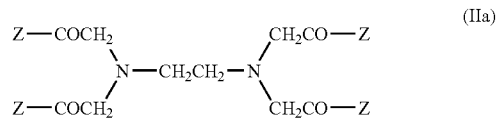

(IIa)

in which the ligand Z is

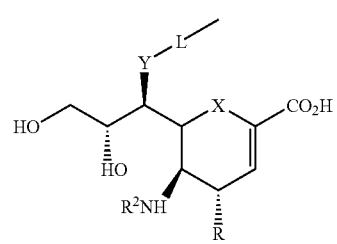

A preferred tetrameric structure is compound (3)
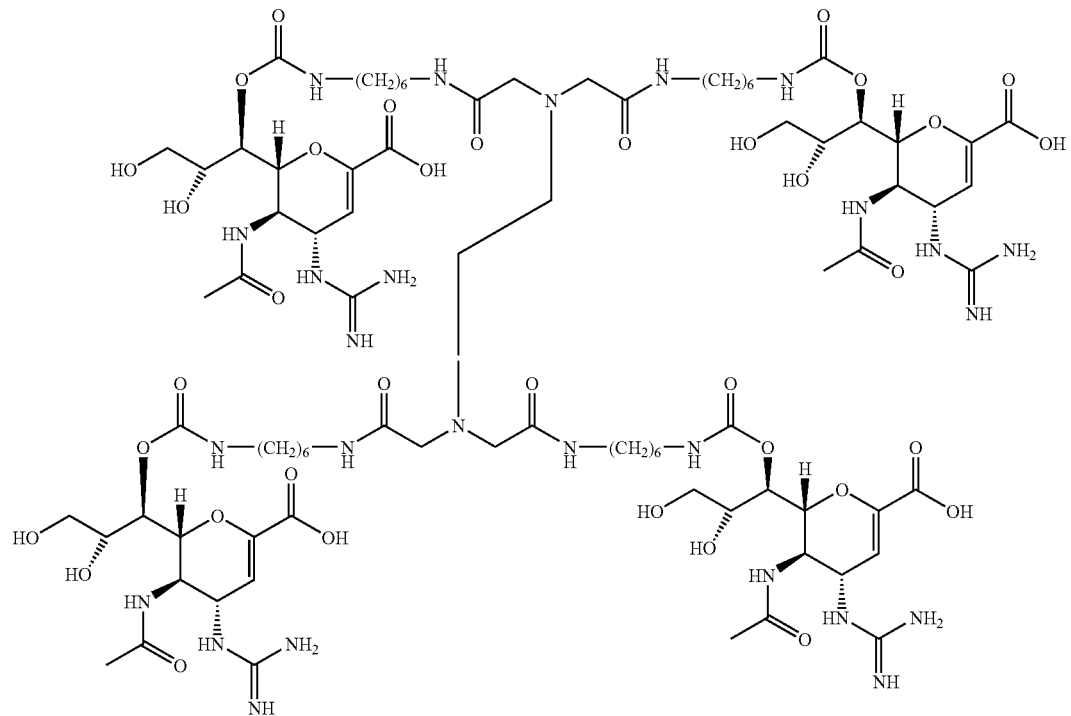
Compound 3
The 32-ligand compound has the structure
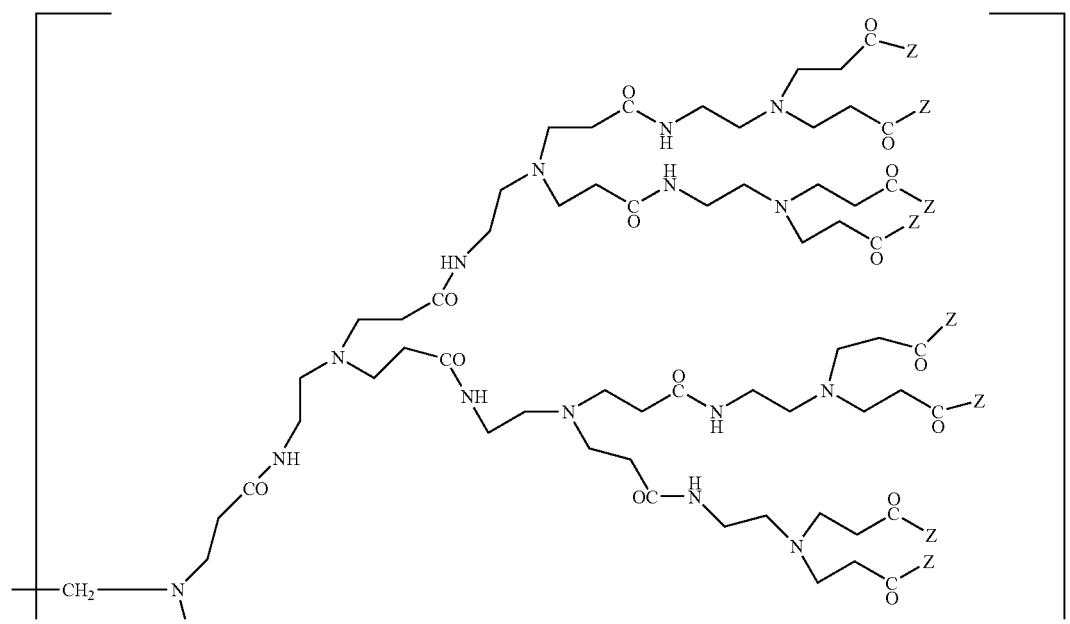

-continued
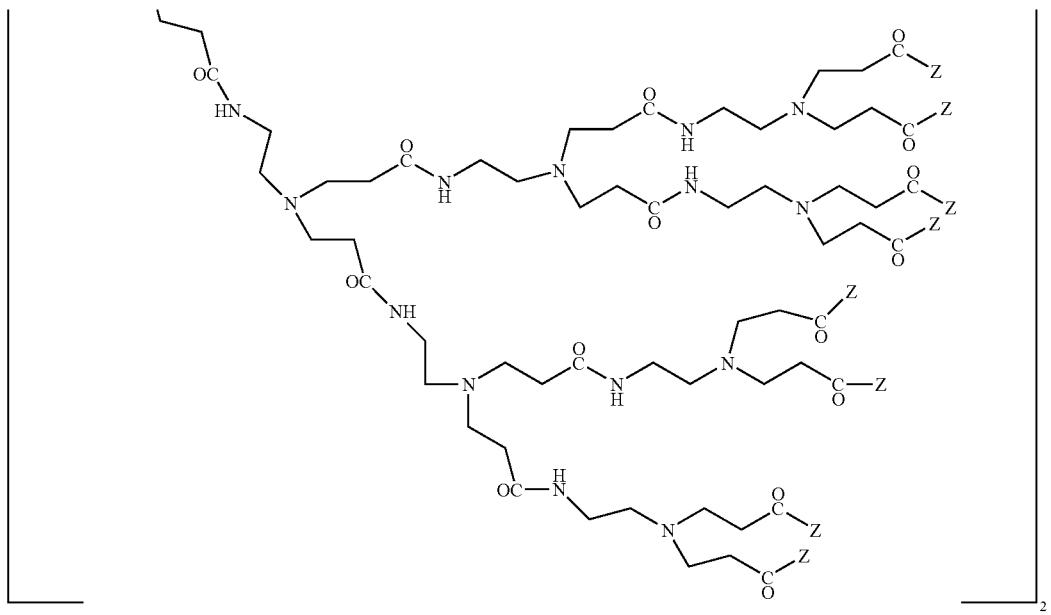
Further preferred compounds are compounds of formula (III):
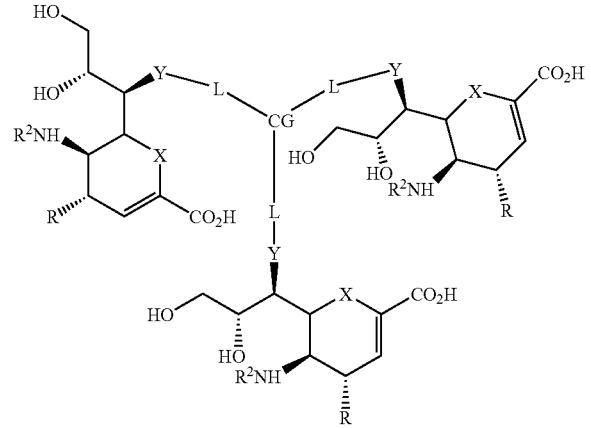
(III)
wherein CG, L, Y, X, R and $R^2$ are as defined for compounds of formula (I).
Other specific examples of compounds of the present invention are set out in Table 1 below.

TABLE 1

| Compound Number (Example No.) | Linker Group L | Multivalent Core Group CG (attached by amide bonds between the CG carbonyl groups and the NH of Linker L) | Number of NA binding groups n |
|---|---|---|---|
| 3 (Example 1) | $NH(CH_2)_6$ | | 4 |
| 4 (Example 2) | $NH(CH_2)_6$ | | 3 |
| 14 (Example 4) | $NH(CH_2)_6$ | | 3 |
| 18 (Example 5) | $NH(CH_2)_6$ | | 4 |
| 19 (Example 5) | $NH(CH_2)_6$ | | 3 |

TABLE 1-continued
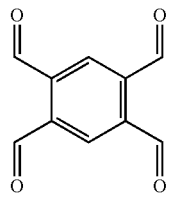
| Compound Number (Example No.) | Linker Group L | Multivalent Core Group CG (attached by amide bonds between the CG carbonyl groups and the NH of Linker L) | Number of NA binding groups n |
|---|---|---|---|
| 20 | $NH(CH_2)_6$ | 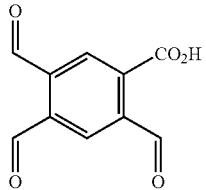 | 4 |
| 21 | $NH(CH_2)_6$ | 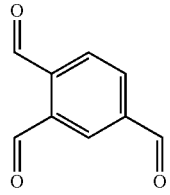 | 3 |
| 22 | $NH(CH_2)_6$ | 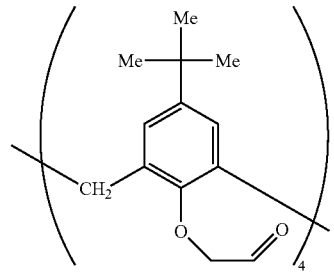 | 3 |
| 23 | $NH(CH_2)_6$ | 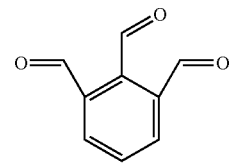 | 4 |
| 24 | $NH(CH_2)_6$ |  | 3 |

TABLE 1-continued
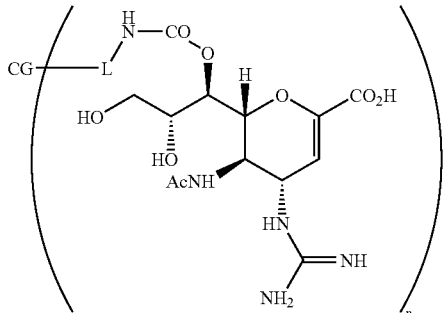
| Compound Number (Example No.) | Linker Group L | Multivalent Core Group CG (attached by amide bonds between the CG carbonyl groups and the NH of Linker L) | Number of NA binding groups n |
|---|---|---|---|
| 25 | NH(CH$_2$)$_6$ | 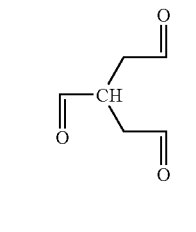 | 3 |
| 26 | NH(CH$_2$)$_6$ | 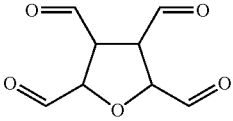 | 3 |
| 27 | NH(CH$_2$)$_6$ | 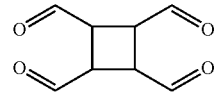 | 4 |
| 28 | NH(CH$_2$)$_6$ | 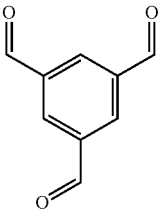 | 4 |
| 29 | NHCH(CO$_2$H)—(CH$_2$)$_4$ | 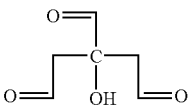 | 3 |
| 31 | NH(CH$_2$)$_6$ | | 3 |

TABLE 1-continued

| Compound Number (Example No.) | Linker Group L | Multivalent Core Group CG (attached by amide bonds between the CG carbonyl groups and the NH of Linker L) | Number of NA binding groups n |
|---|---|---|---|
| 32 | NH(CH$_2$)$_3$ | (1,3,5-benzenetricarbaldehyde) | 3 |

The compounds of the invention may be prepared by the methods outlined below, in which CG, L, Y, X, R and R$^2$ are as defined for formula (I), and W, R$^5$, B, and x are as defined for compounds of formula (II).

Suitable monomeric intermediate compounds of general formula (C) can be prepared following methods described in International Patent Publications No. WO 97/06157 and No. WO 97/32214. Thus if the group at position 7 is an aryl-carbonate (eg. R$^4$=4-nitrophenoxy), the intermediate can be used to make 7-carbamate derivatives (R$^4$=alkyl-NH) by reaction with various amines (alkyl-NH$_2$).

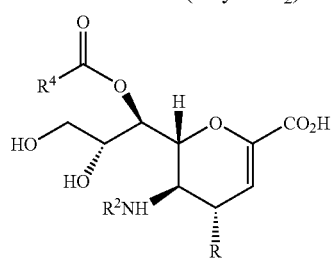

(C)

For example, the (6-aminohexyl)-7-carbamate derivative of GG167, compound (2) below, is a useful precursor to certain compounds of the invention.

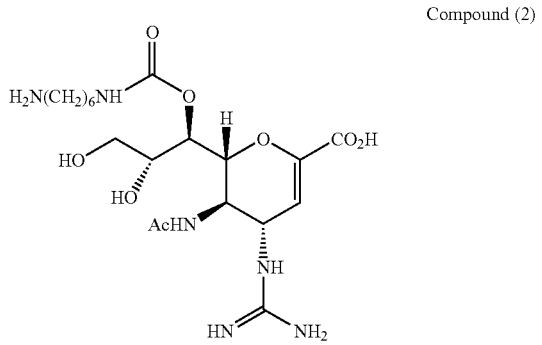

Compound (2)

As will be appreciated by those skilled in the art, it may be necessary or desirable to use protecting groups to protect one or more of the functional groups of the neuraminidase-binding molecule during the process of attaching the monomers to the spacer group. See for example "Protective Groups in Organic Synthesis" by Theodore W. Greene and P. G. M. Wuts (John Wiley & Sons, 1999).

Conventional amino protecting groups may include, for example, arylalkyl groups, such as benzyl, diphenylmethyl or triphenylmethyl groups; and acyl groups, such as N-benzyloxycarbonyl or t-butoxycarbonyl.

Hydroxy groups may be protected, for example, by arylalkyl groups, such as benzyl, diphenylmethyl or triphenylmethyl groups; acyl groups, such as acetyl; silicon protecting groups, such as trimethylsilyl groups; carbonate groups; acetals; or as tetrahydropyran derivatives.

Carboxylic acid groups are conveniently protected as the methyl or diphenylmethyl esters.

Removal of any protecting groups present may be achieved by conventional procedures.

Where it is desired to isolate a compound of the invention as a salt, for example as an acid addition salt, this may be achieved by treating the free base of general formula (I) with an appropriate acid, preferably with an equivalent amount, in a suitable solvent (e.g. aqueous ethanol).

Trimeric and tetrameric compounds of the invention are readily synthesised. It will be appreciated that these can be used as building blocks to make larger compounds, and that compounds in which there is an even number of monomeric units can be formed for example by linking two odd-numbered or two even-numbered multimers, while compounds in which there is an odd number of monomeric units can be formed for example by linking an odd-numbered with an even-numbered multimer.

Compounds of formula (I) may be prepared by coupling compounds of formula (IV);

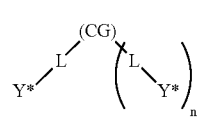
(IV)

wherein Y* is CO₂H, —COLG, NCO, -halide, —OH, —NR³COLG, —OCOLG, —OCSLG, SO₂LG, NR³SO₂LG, NR³CSLG, epoxides, or Michael acceptors, "LG" represents a leaving group, such as halide, or others obvious to those skilled in the art, or protected derivatives thereof;

with compounds of formula (V);

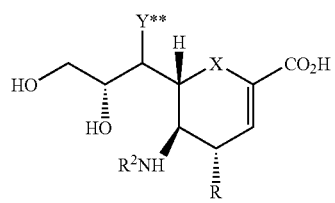
(V)

where Y** represents NHR³ or OH or activated or protected derivatives thereof, followed by de-protection if necessary. This process is referred to herein as method alpha.

Preferably the leaving group is a halide.

Compounds of formula (I) may be prepared by reacting compounds of formula (VI);

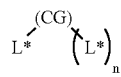
(VI)

wherein L* is L-NHR³, L-OH, L-CO₂H, or protected derivatives thereof, with compounds of formula (VII);

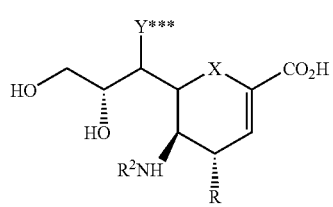
(VII)

wherein Y*** represents D-AG or halogen;

D represents O or NR³;

AG represents COLG, H, CSLG or SO₂LG;

and LG represent a leaving group such as a halide, or others obvious to those skilled in the art, or protected derivatives thereof. This process is called method beta.

Compounds of formula (II) may be prepared by coupling compounds of formula (VIII);

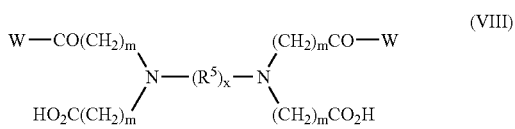
(VIII)

or protected derivatives thereof, with compounds of formula B—Y-L-H, or protected derivatives thereof, wherein B, Y, and L are as defined in formula (II), and the atom in L bonded to H is a heteroatom;

followed by deprotection if necessary.

Compounds of formula (VIII) may be prepared by reacting compounds of formula W—H, where W is as defined in formula (II), or protected derivatives thereof, with compounds of formula (IX);

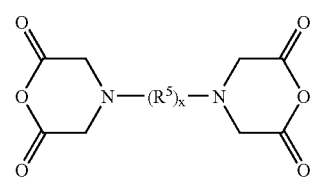
(IX)

Compounds of formula (IX) may be prepared by a cyclisation reaction of compounds of formula (X).

Many compounds of formula (X) are commercially available, for example EDTA.

An alternative process for the preparation of compounds of formula (II) is a coupling of compounds of formula (V), or protected derivatives thereof, with compounds of formula (XI):

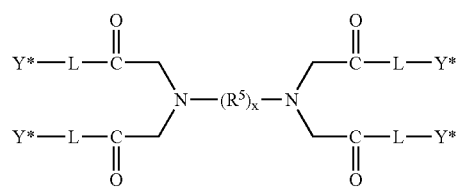
(XI)

by method alpha described above, followed by deprotection if necessary.

An alternative process for the preparation of compounds of formula (II) wherein the terminal atom in L is nitrogen, is coupling of compounds of formula (XII):

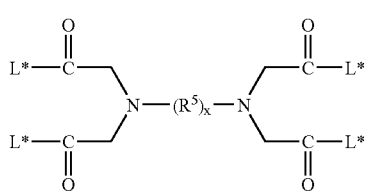
(XII)

or protected derivatives thereof, with compounds of formula (VII), or protected derivatives thereof, by method beta described above, followed by deprotection if necessary.

A further process for the production of compounds of formula (II) wherein $R^5$ is a substituted or unsubstituted alkyl group comprises reaction of compounds of formula (XIII):

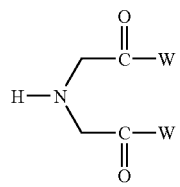

(XIII)

wherein W is as defined for compounds of formula (II), or protected derivatives thereof, with a substituted or unsubstituted alkyl halide, for example $BrCH_2CH_2Br$, followed by deprotection if necessary.

Compounds of formulae (XI) and (XII) may be prepared by reacting compounds of formula L* or L-Y* with compounds of formula (X) or formula (IX).

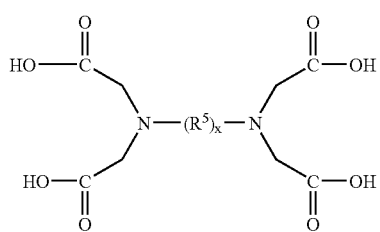

(X)

Compounds of formula (XIII) may be prepared by a peptide/carbonate/mixed anhydride coupling of W, where W is not OH or $N(R^3)_2$, with a compound of formula (XIV):

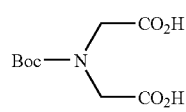

(XIV)

wherein W is as defined for compounds of formula (II).

Compounds of formula (XIV) are commercially available. It will be appreciated by those skilled in the art that the pharmaceutically acceptable derivatives of the compounds of formula (I) may be derivatised at more than one position.

The term "pharmaceutically acceptable derivative" means any pharmaceutically acceptable salt, ester or salt of such ester of a compound of formula (I) or any other compound which, upon administration to the recipient, is capable of providing a compound of formula (I) or an anti-virally active metabolite or residue thereof. Of particular interest as derivatives are compounds modified at the sialic acid carboxy or glycerol hydroxy groups, or at the amino and guanidino groups.

Pharmaceutically acceptable salts of the compounds of formula (I) include those derived from pharmaceutically acceptable inorganic and organic acids and bases. Examples of suitable acids include hydrochloric, hydrobromic, sulphuric, nitric, perchloric, fumaric, maleic, phosphoric, glycolic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic acid, while not in themselves pharmaceutically acceptable, may be useful in the preparation of salts useful as intermediates in obtaining compounds of the invention and their pharmaceutically acceptable acid addition salts.

Salts derived from appropriate bases include alkali metal (eg. sodium), alkaline earth metal (eg. magnesium), ammonium, and $NR_4^+$ (where R is $C_{1-4}$alkyl) salts.

Compounds of formula (I) or (II) can be converted into other compounds of formula (I) or (II) respectively by reactions known in the art, for example hydrolysis or acidolysis of protecting groups to reveal hydroxy or carboxy groups or deprotection of protected amines or guanidines. Conversion of an amine group to a guanidino group can also be carried out by processes known in the art.

The compounds of the invention possess antiviral activity. In particular these compounds are inhibitors of viral neuraminidase of orthomyxoviruses and paramyxoviruses, for example the viral neuraminidase of influenza A and B, parainfluenza, mumps and Newcastle disease.

Thus in a second aspect the invention provides a compound of formula (I) or a pharmaceutically acceptable derivative thereof for use as an active therapeutic agent in the treatment and/or prophylaxis of orthomyxovirus and paramyxovirus infections.

In a third aspect the invention provides a method for the treatment and/or prophylaxis of a viral infection, for example orthomyxovirus or paramyxovirus infection in a subject, comprising the step of administration of an effective amount of a compound of of the invention or a pharmaceutically acceptable derivative thereof to a subject in need of such treatment.

Preferably the subject is an animal such as a mammal, and more preferably a human.

The mammal may be a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, cattle, and sheep or birds such as chickens, ducks or geese, or zoo animals such as felids, canids, bovids, and ungulates.

In a preferred embodiment, this aspect of the invention provides a method for the treatment and/or prophylaxis of influenza A or B infection in a mammal, comprising the step of administration of an effective amount of a compound of the invention or a pharmaceutically acceptable derivative thereof to a subject in need of such treatment. Preferably the subject is a human.

In a fourth aspect the invention provides the use of a compound of the invention or a pharmaceutically acceptable derivative thereof for the manufacture of a medicament for the treatment or prophylaxis of a viral infection.

The compounds of the invention may also be used in diagnostic methods, in particular methods for the detection of influenza virus. For use in such methods it may be advantageous to link a compound of the invention to a label, such as a radioactive, fluorescent, or chemiluminescent label. The person skilled in the art will be aware of a wide variety of suitable labels. Methods of diagnosis for which the compounds of the invention are suitable are described, for example, in our earlier applications PCT/AU97/00109 and PCT/AU97/00771.

In a fifth aspect the invention provides a method for the detection of a viral infection which comprises the step of contacting the compound of the invention with a sample suspected of containing the virus.

It will be further appreciated that the amount of a compound of the invention required for use in treatment and/or prophylaxis will vary not only with the particular compound selected, but also with the route of administration, the nature of the condition being treated, and the age and condition of the patient, and will ultimately be at the discretion of the attendant physician or veterinarian. In general however, a suitable dose will be in the range of from about 0.0001 to 100 mg/kg of bodyweight per day, preferably in the range of 0.0001 to 20 mg/kg/day, even more preferably in the range of 0.002 to 1.0 mg/kg/day.

For treatment, the compounds are effective when given post-infection; for example after the appearance of established symptoms. For prophylaxis, the compounds are effective when given before or at the time of exposure to infection.

Suitably treatment is given 1–2 times fortnightly, 1–2 weekly or 1–4 times daily, and continued for 3–7 days post-infection, eg. 5 days, depending upon the particular compound used. Preferably treatment is given once or twice a week. Even more preferably treatment is a single dose.

The desired dose may be presented in a single dose per week, or as divided doses administered at appropriate intervals, for example as two, three, four or more sub-doses per day.

Preferably for treatment of infection the compound is administered once or twice a week, most preferably in a single dose immediately after diagnosis of infection. For example, using the diagnostic method described in our earlier applications, PCT/AU97/00109 and PCT/AU97/0077, it would be possible to diagnose infection with influenza in the physician's office, and provide treatment immediately.

The long-lasting lung residence properties of the compounds of the invention confirm the advantage that treatment may only need to be given once weekly.

A further aspect of the invention is a method of treatment and/or prophylaxis of influenza A or B, comprising administering of an effective amount of a discrete multimeric compound which comprises three or more neuramindase binding groups wherein the administration occurs once. Preferably the discrete multimeric compound is a compound of formula (I) or a pharmaceutically acceptable derivative thereof.

For prophylactic purposes, the compound is administered once or twice per week or once each 2 to 3 weeks, preferably once a week.

The compound is conveniently administered in unit dosage form, for example containing 0.05 to 500 mg, conveniently 0.01 to 50 mg, most conveniently 0.1 to 20 mg of active ingredient per unit dosage form.

While it is possible that, for use in therapy or prophylaxis, a compound of the invention may be administered as the raw chemical, it is preferable to present the active ingredient as a pharmaceutical composition.

Thus in a sixth aspect the invention provides a pharmaceutical composition comprising a compound of formula (I) or a pharmaceutically acceptable derivative thereof, together with one or more pharmaceutically acceptable carriers thereof and, optionally, one or more other therapeutic and/or prophylactic ingredients. The carrier(s) must be "acceptable" in the sense of being compatible with the other ingredients of the formulation and not being deleterious to the recipient thereof.

The compounds of the invention may also be used in combination with other therapeutic agents, for example other anti-infective agents. In particular the compounds of the invention may be employed with other antiviral agents. Thus in a seventh aspect the invention provides a combination comprising a compound of formula (I) or a pharmaceutically acceptable derivative thereof together with another therapeutically active agent, in particular an antiviral agent.

The combinations referred to above may conveniently be presented for use in the form of a pharmaceutical composition, and thus such compositions comprising a combination as defined above together with a pharmaceutically acceptable carrier therefor represent a further aspect of the invention.

Suitable therapeutic agents for use in such combinations include other anti-infective agents, in particular anti-bacterial and anti-viral agents such as those used to treat respiratory infections. For example, other compounds effective against influenza viruses, such as amantadine, rimantadine and ribavirin, and the sialic acid analogues referred to above, may be included in such combinations.

The individual components of such combinations may be administered either sequentially or simultaneously, in separate or combined pharmaceutical formulations.

When the compounds of the invention are used with a second therapeutic agent active against the same virus, the dose of each compound may either be the same as or different from that employed when each compound is used alone. Appropriate doses will be readily appreciated by those skilled in the art.

Pharmaceutical formulations include those suitable for oral, nasal, topical (including buccal and sublingual), or parenteral (including intramuscular, subcutaneous and intravenous) administration, or those in a form suitable for administration to the respiratory tract (including the nasal passages) for example by inhalation or insufflation. The formulations may, where appropriate, be conveniently presented in discrete dosage units, and may be prepared by any of the methods well known in the art of pharmacy. These methods include the step of bringing the active compound into association with liquid carriers or finely divided solid carriers or both, and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may-also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may for example be in the form of aqueous or oily suspensions, solutions, emulsions, syrups, colloidal dispersions or elixirs, or may be presented as a dry product for constitution with water or other suitable vehicle before use. Such liquid preparations may contain conventional additives such as suspending agents, emulsifying agents, non-aqueous vehicles, which may include edible oils, or preservatives.

The compounds according to the invention may also be formulated for parenteral administration by injection, for example bolus injection, or continuous infusion, and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulating agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Formulations suitable for topical administration in the mouth include lozenges comprising active ingredient in a flavoured base, usually sucrose and gum acacia or gum tragacanth; pastilles comprising the active ingredient in an inert base such as gelatin or sucrose and gum acacia; and mouthwashes comprising the active ingredient in a suitable liquid carrier.

For administration to the respiratory tract by inhalation, insufflation and intranasal administration, the neuraminidase inhibitors may be administered by any of the methods and formulations employed in the art for administration to the respiratory tract.

Thus in general for administration to the respiratory tract the compounds may be administered in the form of a solution or a suspension or as a dry powder.

Solutions and suspensions will generally be aqueous, for example prepared from water alone (for example sterile or pyrogen-free water) or water and a physiologically acceptable co-solvent (for example ethanol, propylene glycol or polyethlene glycols such as PEG 400).

Such solutions or suspensions may additionally contain other excipients for example preservatives (such as benzalkonium chloride), solubilising agents/surfactants such as polysorbates (eg. Tween 80, Span 80, benzalkonium chloride), buffering agents, isotonicity-adjusting agents (for example sodium chloride), absorption enhancers and viscosity enhancers. Suspensions may additionally contain suspending agents (for example microcrystalline cellulose, carboxymethyl cellulose sodium).

Solutions or suspensions are applied directly to the nasal cavity by conventional means, for example with a dropper, pipette or spray. The formulations may be provided in single or multidose form. In the latter case a means of dose metering is desirably provided. In the case of a dropper or pipette this may be achieved by the patient administering an appropriate, predetermined volume of the solution or suspension. In the case of a spray this may be achieved for example by means of a metering atomising spray pump.

Administration to the respiratory tract may also be achieved by means of an aerosol formulation in which the compound is provided in a pressurised pack with a suitable propellant, such as a chlorofluorocarbon (CFC), for example dichlorodifluoromethane, trichlorofluoromethane or dichlorotetrafluoroethane, carbon dioxide or other suitable gas. The aerosol may conveniently also contain a surfactant such as lecithin. The dose of drug may be controlled by provision of a metered valve.

Alternatively the compounds may be provided in the form of a dry powder, or a dry powder mix, for example a powder mix of the compound in a suitable powder base such as lactose, starch, starch derivatives such as hydroxypropylmethyl cellulose and polyvinylpyrrolidine (PVP). The powder composition may be presented in unit dose form, for example in capsules or cartridges of eg. gelatin, or blister packs from which the powder may be administered by means of an inhaler.

In formulations intended for administration to the respiratory tract, including intranasal formulations, the compound will generally have a small particle size, for example of the order of 5 microns or less (mass median aerodynamic diameter). Such a particle size may be obtained by means known in the art, for example by micronisation.

Preferably the compounds of the invention are administered to the respiratory tract by inhalation, insufflation or intranasal administration, or a combination thereof.

"Relenza" is administered by oral inhalation as a free-flow powder via a "Diskhaler" (trade mark of Glaxo Wellcome plc). A similar formulation would be suitable for the present invention.

Thus, according to a still further aspect of the present invention there is provided an inhaler which contains a composition as defined above.

It will be appreciated that the inhaler may also be in the form of a meter dose aerosol inhaler.

When desired, formulations adapted to give sustained release of the active ingredient may be employed.

DETAILED DESCRIPTION OF THE INVENTION

The invention will now be described in detail by way of reference only to the following non-limiting examples.

EXAMPLE 1

Preparation of an ethylenediaminetetraacetamido derivative (3) of 5-acetamido-7-(6-aminohexylcarbamoyloxy)-4-guanidino-2,3,4,5-tetradeoxy-D-glycero-D-galacto-non-2-enopyranosonic acid [Tetramer of Compound (2)]

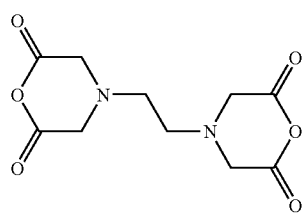

1. Compound 1, Pyridine, DMF

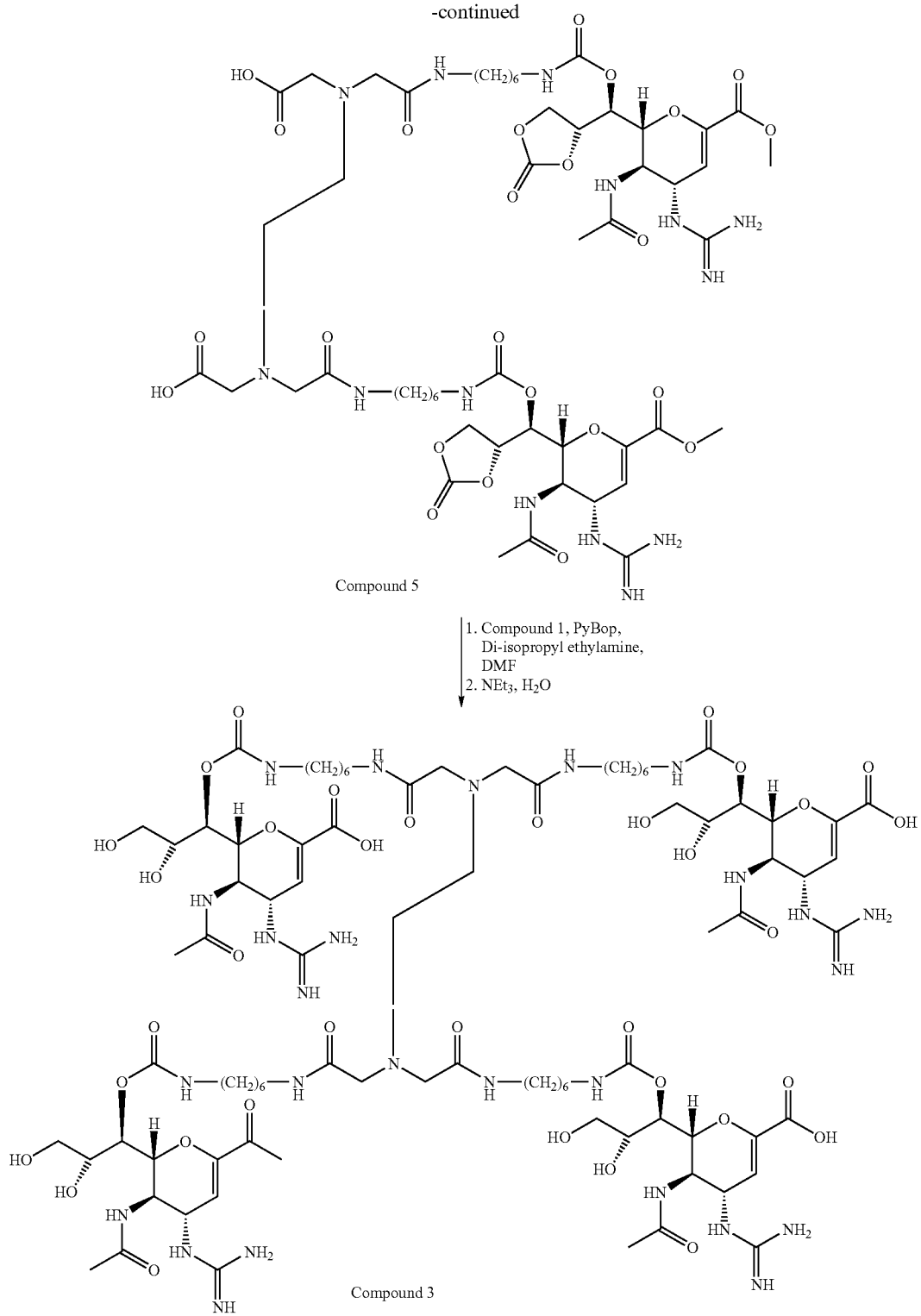

Compound 5

1. Compound 1, PyBop, Di-isopropyl ethylamine, DMF
2. NEt₃, H₂O

Compound 3

The 7-carbamate derivative (2a) was prepared following a similar procedure to that described in our earlier patent application PCT/AU97/00109.

Compound (2a) (40 mg, 5.39×10⁻⁵ mole), ethylenediaminetetraacetic acid dianhydride (7 mg, 2.69×10⁻⁵ mole) and pyridine (6.8 μl, 8.07×10⁻⁵ mole) were stirred in dimethylformamide (200 μl) at 50° C. for 3 h. The reaction mixture was co-evaporated with toluene to afford compound (5) as a white foam (44 mg).

LC R$_t$ 2.1 min, MS 643 [M+2H]$^{2+}$, (method A);

TOF 643.3 [M+2H]$^{2+}$, 1285.5 [M+H]$^+$, (method B),

To a solution of dimer (5) (200 mg, 1.557×10$^{-4}$ mole) in dimethylformamide (3 ml) was added benzotriazol-1-yloxy tris(pyrrolidino)phosphonium hexafluorophosphate (162 mg, 3.12×10$^{-4}$ mole), compound (2) (231 mg, 3.12×10$^{-4}$ mole) and diisopropylethylamine (241 µl, 1.557×10$^{-3}$ mole). The reaction mixture was stirred overnight at room temperature before evaporation to dryness. The crude product was purified by preparative HPLC (method C) to afford the protected form of the title compound. (250 mg) as the trifluoroacetic acid salt. LC $R_t$ 2.4 min (method A), MS TOF 759.9 [M+3H]$^{3+}$, 1139.3 [M+2H]$^{2+}$, 2277.5 [M+H]$^{+}$, (method B). This compound (100 mg) and triethylamine (3 ml) in water were stirred at room temperature for 1 h. before evaporation to dryness. The crude product was purified by preparative HPLC (method D) to afford the title compound (20 mg) as the trifluoroacetic acid salt.

LC $R_t$ 5.4 min, MS TOF 530.2 [M+4H]$^{4+}$, 706.6 [M+3H]$^{3+}$, 1059.4 [M+2H]$^{2+}$, (method B).

Method A (LC/MS)

Micromass Platform II mass spectrometer operating in positive ion electrospray mode, mass range 100–1000 amu.
Column: 3.3 cm×4.6 mm ID, 3 um ABZ+PLUS
Flow Rate: 3 ml/min
Injection Volume: 5 µl
Solvent A: 95% Acetonitrile+0.05% Formic Acid
Solvent B: 0.1% Formic Acid+10 mMolar Ammonium Acetate
Gradient: 0–100% A/5 min, 100–0% B/5 min Method B TOF (LC/MS)

The TOF instrument is a Micromass LCT mass spectrometer operating in positive ion electrospray mode, mass range 100–3000 amu. Continuum data acquisition mode.
The HPLC gradient method uses
Column: 15 cm×2.1 mm ID, 3.5 um Xterra (Waters)
Flow Rate: 0.4 ml/min
Injection Volume: 5 µl
Solvent A: 100% Acetonitrile+0.05% Formic acid
Solvent B: 0.1% Formic Acid
Gradient: 15% A/10 min, 85% B/10 min then 15–100% A/10 min, 85–0% B/10 min Method C The Prep column used was a Supelcosil ABZplus (10 cm×2.5 cm).
uv wavelength: 230 nm
Flow: 4 ml/min
Solvent A: Acetonitrile (+0.05% TFA)
Solvent B: water (+0.1% TFA)
Gradient: 5–50% A/20 min, 95–50% B/20 min then 50–95% A/10 min, 50–5% B/10 min.

Method D

The Prep column used was a Supelcosil ABZplus (10 cm×2.5 cm).
uv wavelength: 230 nm
Flow: 4 ml/min
Solvent A: Acetonitrile (+0.05% TFA)
Solvent B: water (+0.1% TFA)
Gradient: 15% A/20 min, 85% B/20 min then 15–95% A/10 min, 85–5% B/10 min.

EXAMPLE 2

Preparation of the Trimer (4) from 1,3,5-Benzenetricarboxylic (Trimesic) Acid and Compound (2a)

Mass spectrometry was performed on a Micromass Platform II mass spectrometer with electrospray ionisation and positive ion detection. RP-HPLC purification was performed with a Gilson HPLC system comprising of a Gilson 322 pumping system, a Gilson 215 Fraction Collector and a Hewlett Packard 1100 Photodiode Array Detector. The purified yields for compounds 4a and 4 have been calculated based on the molecular weight of a tris-trifluoroacetic acid complex.

Synthesis

Reaction A

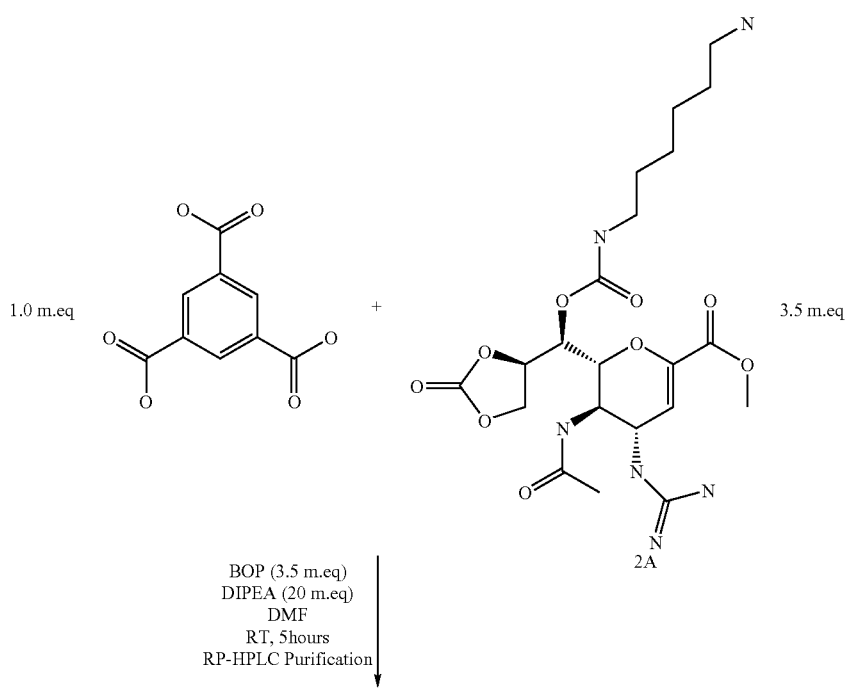

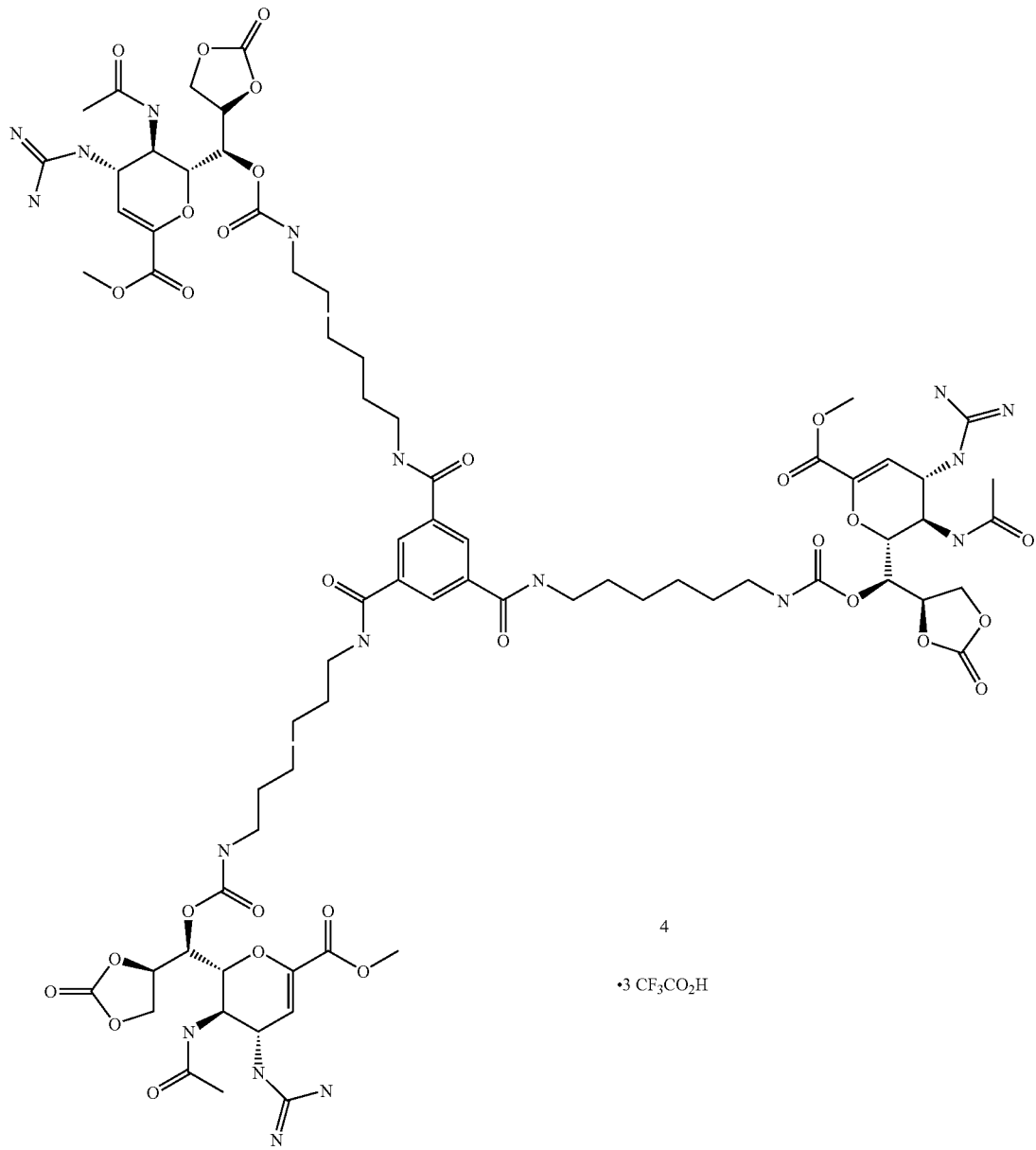

4

•3 CF$_3$CO$_2$H

Compound 2a (62.0 mg, 8.33×10$^{-5}$ mol), trimesic acid (I) (5.0 mg, 2.38×10$^{-5}$ mol) and benzotriazol-1-yloxy-tris(dimethylamino)phosphonium hexafluorophosphate (BOP) (37.0 mg, 8.33×10$^{-5}$ mol) were dissolved in DMF (2 mL) and stirred at room temperature. Diisopropylethyl amine (90 ul, 5.16×10$^{-5}$ mol) was then added to the above solution and the solution was allowed to stir at room temperature for 5 hours. The crude solution was then purified, with no additional workup, using C18 RP-HPLC to yield the desired product (4) (17.9 mg, 8.77×10$^{-6}$ mol) in 37% yield.

$^1$H n.m.r. (CD$_3$OD): δ 1.45 (br, 12H), 1.54–1.58 (m, 6H) 1.69–1.72 (br, 6H), 1.98 (s, 9H), 3.00–3.25 (m, 6H), 3.46 (t, 6.9 Hz, 6H), 3.84 (s, 9H), 4.17 (t, 10.0 Hz, 3H), 4.47 (dd, 9.3 Hz, 2.2 Hz, 6H), 4.70–4.80 (m, 6H), 5.18, (m, 3H), 5.62 (t, 2.4 Hz, 3H), 5.93 (d, 2.4 Hz, 3H), 8.41 (s, 3H), m/z 568 ([M+3H]$^{3+}$, 85%), 851 ([M+2H]$^{2+}$, 100%), 907 ([M+CF$_3$CO$_2$H+2H]$^{2+}$, 30%).

Purification of Compound 4a

The RP-HPLC purification of compound 4a was performed with a binary solvent system (A=Water with 0.1% TFA, B=Acetonitrile with 0.06% TFA) using a Waters Symmetry C-18, 5 micron, 19×100 mm column. The following gradient was used:

| Time | A % | B % | Flow |
| --- | --- | --- | --- |
| 0.00 | 100 | 0 | 6 |
| 2.00 | 100 | 0 | 6 |
| 22.00 | 40 | 60 | 6 |
| 32.00 | 40 | 60 | 6 |
| 35.00 | 100 | 0 | 6 |
| 43.00 | 100 | 0 | 6 |

Reaction B:

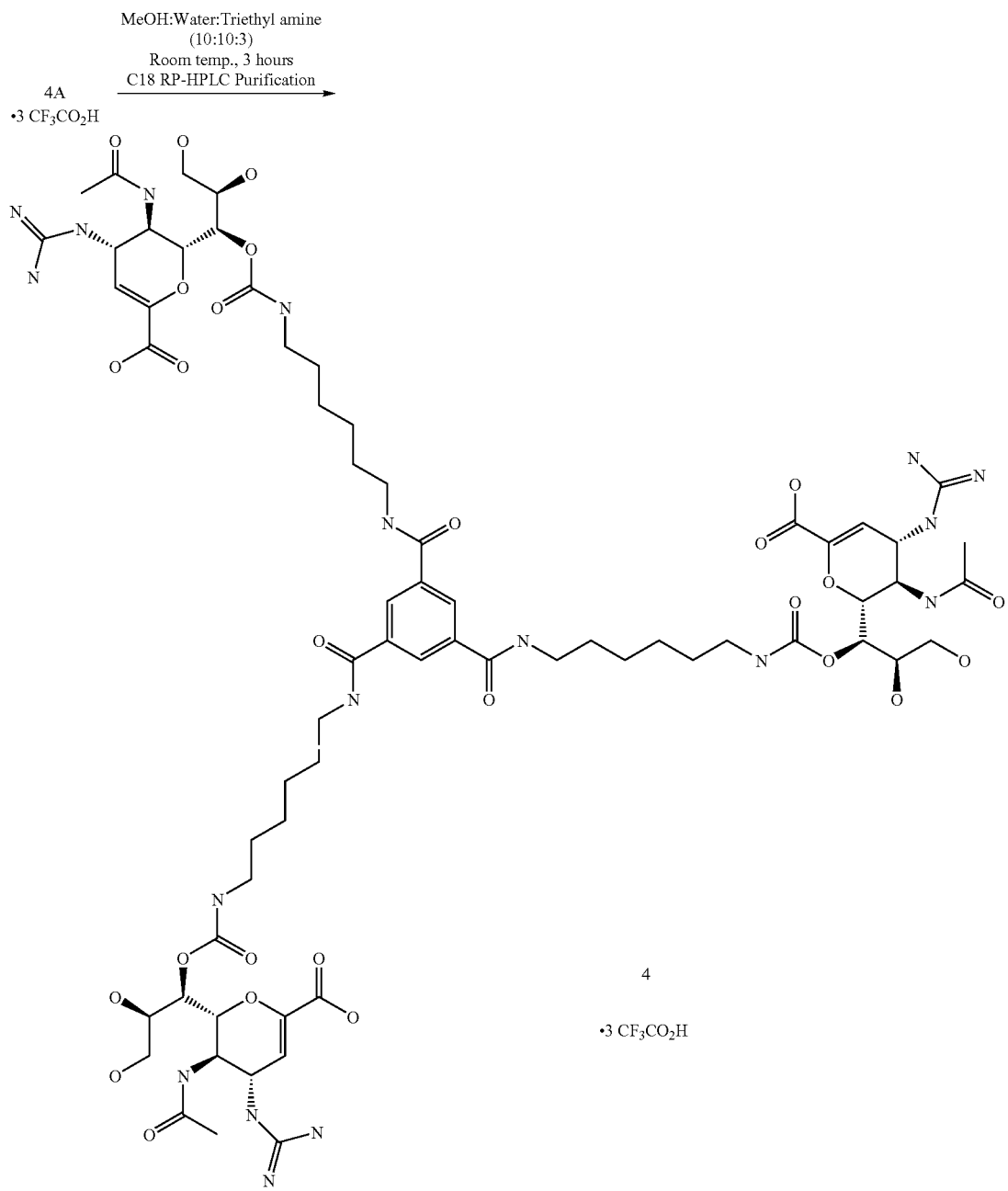

Molecular Weight = 1921.71

Compound 4a (14.4 mg, 7.05×10⁻⁶ mol) was dissolved in 6 mL of a solution containing methanol, water and triethyl amine in a ratio of 10:10:3 respectively. The solution was allowed to stir at room temperature for 3 hours. The solvent was then removed under reduced pressure. The excess triethyl amine was removed by azeotroping with water under reduced pressure. The crude material was then purified using C18 RP-HPLC to yield the desired product 4 (8.11 mg, 4.22×10⁻⁶ mol) in 60% yield.

$^1$H n.m.r. (CD$_3$OD): δ 1.47 (br, 12H), 1.54–1.58 (m, 6H), 1.70–1.75 (m, 6H), 2.00 (s, 9H), 3.00–3.20 (m, 6H), 3.47 (t, 7.1 Hz, 6H), 3.50–3.56, (m, 3H), 3.69 (dd, 11.8 Hz, 3.1 Hz, 3H), 4.0–4.1 (m, 3H), 4.24 (t, 9.3 Hz, 3H), 4.41 (dd, 8.7 Hz, 2.5 Hz, 3H), 4.59 (dd, 9.6 Hz, 2.4 Hz, 3H), 5.03 (dd, 9.2 Hz, 2.3 Hz, 3H), 5.92, (d, 2.6 Hz, 3H), 8.42 (s, 3H), m/z 528 ([M+3H]$^{3+}$, 35%), 790 ([M+2H]$^{2+}$, 1054 ([2M+3H]$^{3+}$, 35%), 1579 ([M+H]$^{1+}$, 20%).

Purification of Compound 4

The RP-HPLC purification of compound 2a was performed with a binary solvent system (A=Water with 0.1%

TFA, B=Acetonitrile with 0.06% TFA) using a Waters Symmetry C-18 5 micron 19×100 mm column. The following gradient was used:

| Time | A % | B % | Flow |
|---|---|---|---|
| 0.00 | 100 | 0 | 6 |
| 2.00 | 100 | 0 | 6 |
| 22.00 | 60 | 40 | 6 |
| 32.00 | 60 | 40 | 6 |
| 35.00 | 100 | 0 | 6 |
| 43.00 | 100 | 0 | 6 |

EXAMPLE 3

Alternative Synthesis of Tetramer (Compound (3))

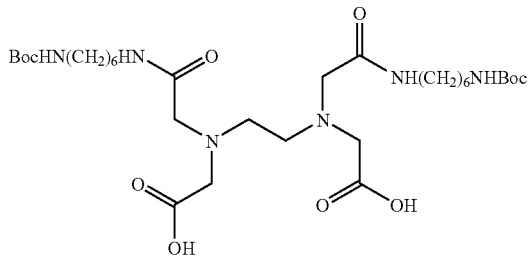

Compound (6)

Ethylenediaminetetraacetic dianhydride (2.36 g), N-(6-aminohexyl)carbamic acid t-butyl ester (4.00 g), pyridine (1.9 mL) and dimethylformamide (10 mL) were stirred at room temperature overnight followed by warming to 55° C. for 3 h. The solvent was then removed in vacuo and azeotroped with toluene (3×25 mL) to afford Compound (6) (6.3 g).
Mass spec. MH+ 689

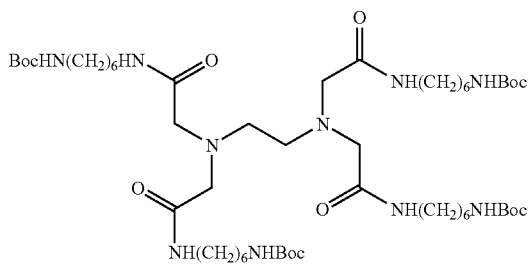

Compound (7)

Compound (6) (500 mg, 0.73 mmol) was dissolved in anhydrous dimethylformamide (2.0 mL). Diisopropylethylamine (1.0 mL), Hydroxybenzotriazole (194 mg) and benzotriazol-1-yloxytris(pyrrolidino)phosphonium hexafluorophosphate (760 mg) were added consecutively. The reaction was stirred under a nitrogen atmosphere at room temperature for 15 minutes. N-(6-aminohexyl)carbamic acid t-butyl ester hydrochloride (405 mg) was added and the reaction stirred at room temperature overnight. Solvent was removed in vacuo, and the residue redissolved in 1:1 v/v diethyl ether: ethyl acetate (30 mL). This solution was washed with saturated aqueous sodium bicarbonate then brine (both 30 mL). Solvent was removed in vacuo to give a crude yellow oil. The crude product was purified by chromatography on silica gel, using a 20 g solid phase extraction cartridge. Compound (7) was eluted by 100:8:1 v/v dichloromethane:ethanol:NH$_3$. Removal of solvent in vacuo gave Compound (7) as a white foam (288 mg). TLC SiO$_2$ (100:8:1 dichloromethane:ethanol:NH$_3$) R$_f$ 0.15.

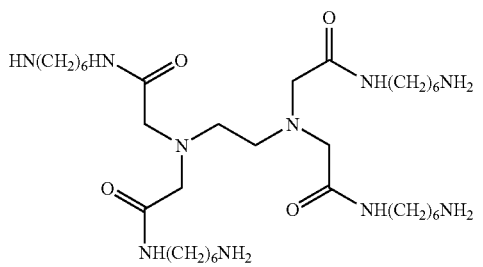

Compound (8)

Compound (7) (0.28 g) was stirred with trifluoroacetic acid (5 mL) for 45 min and then concentrated in vacuo to afford Compound (8) (0.423 g).

$^1$H-NMR (d6-DMSO); δ 1.24 (m, 16H), 1.38 (m, 8H), 1.48 (m, 8H), 2.74 (broad s, 8H), 3.07 (m, 12H), 3.90–4.60 (broad s), 7.78 (broad s, 8H), 8.26 (t, 4H).

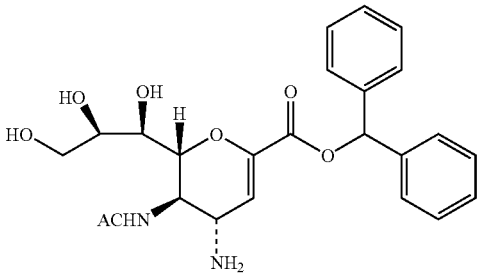

Compound (9)

(2R,3R,4S)-3-(Acetylamino)-4-amino-2-[(1R,2R)-1,2,3-trihydroxypropyl]-3,4-dihydro-2H-pyran-6-carboxylic acid trihydrate (85 g, 0.247 mol) was suspended in methanol (700 mL). Diphenyldiazomethane solution in dichloromethane (200 mL, 0.092 mol) and 2M aqueous hydrochloric acid (3 mL) were added. The suspension was stirred at room temperature for 15 hours. More 2M aqueous hydrochloric acid (10 ml) was added and the suspension stirred for 5 hours. More diphenyldiazomethane solution in dichloromethane (300 mL, 0.15 mol) was added and the suspension stirred for 15 hours. The solid was removed by filtration and the filtrate evaporated in vacuo. The material was purified using silica SPE cartridges, eluting with dichloromethane, acetonitrile, acetonitrile/methanol/water 20:5:1, acetonitrile/methanol/water 20:5:2. The solvent was evaporated in vacuo to leave Compound (9) as an off-white solid. (22 g)

MH+ found 457

MH+ found 699

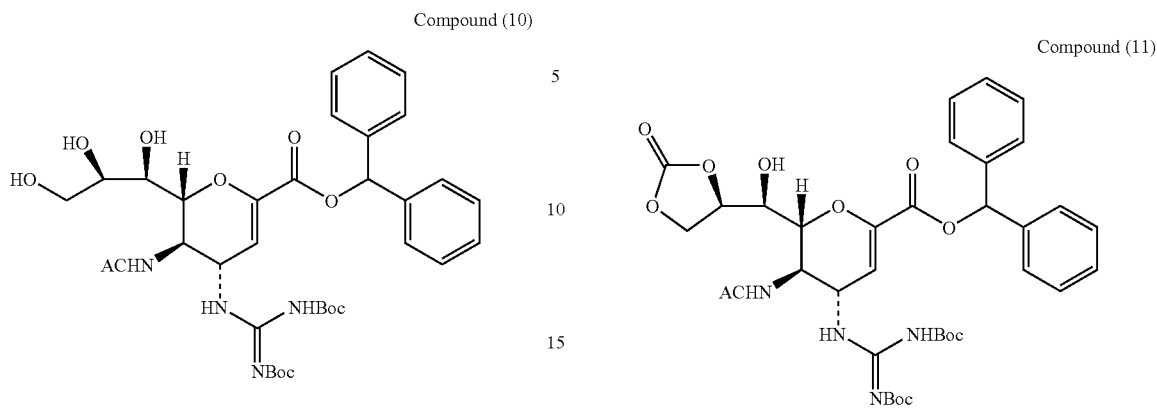

Compound (10)

Compound (11)

Compound (9) (13.67 g, 30 mmol) was dissolved in methanol (100 mL) and N,N'-bis-tert-butoxycarbonyl-1-guanyl pyrazole (10.22 g, 32.9 mmol) added. The reaction was stirred at room temperature for 48 hours. The volatiles were removed in vacuo. The residue was stirred and shaken with dichloromethane (100 mL) for 20 minutes, and the insoluble material removed by filtration. The filtrate was concentrated and purified using flash column chromatography on silica eluting with ethyl acetate/cyclohexane 1:1 followed by ethyl acetate. The product containing fractions were evaporated in vacuo to leave Compound (10) as a white solid. (8.2 g)

Compound (10) (11.0 g, 1.4 mmol) was dissolved in anhydrous acetonitrile (10 mL). Carbonyl diimidazole (280 mg) was added, and the reaction stirred under nitrogen at room temperature for 3.5 hours. Solvent was removed in vacuo to give a clear viscous residue. The crude product was purified by chromatography on silica gel, using a 20 g solid phase extraction cartridge. Compound (11) was eluted by 1:1 v/v ethyl acetate: cyclohexane. Removal of solvent in vacuo gave Compound (11) as a white crystalline solid (747 mg). TLC $SiO_2$ (ethyl acetate) $R_f$ 0.7

Mass spec: 725 m/z (MH+)

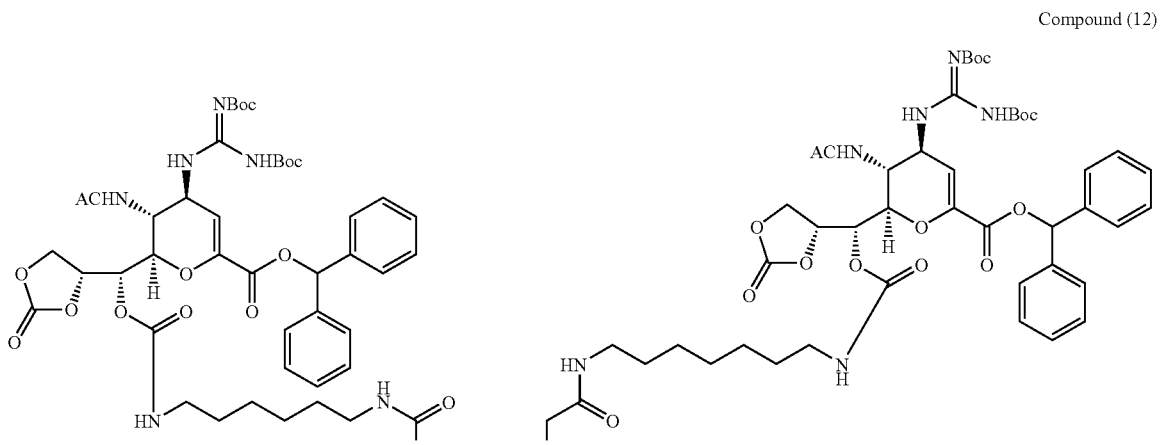

Compound (12)

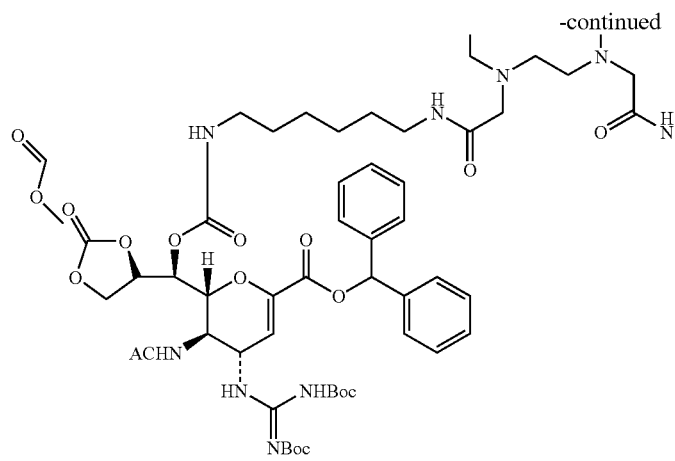
-continued

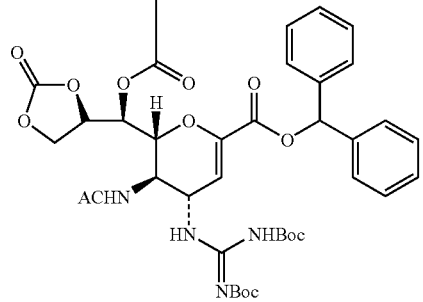

To Compound (11) (0.067 g) was added acetonitrile (0.5 mL), 4-dimethylaminopyridine (0.034 g), N,N'-succininidyl carbonate (0.036 g), and the mixture stirred at room temperature for 3 days. To this mixture was added Compound (8) (0.085 g), diisopropylethylamine (0.16 mL) and acetonitrile (0.5 mL) and the mixture stirred at room temperature for 3 days, yielding a mixture comprising Compound (12).

Mass Spec. M/3=1229

The protecting groups are then cleared by conventional methods to yield the free tetramer, Compound (3).

EXAMPLE 4
Preparation of the Trimer (14) from EDTA and Compound (2a)

Intermediate (13)

Compound (5) (0.0766 g), benzotriazol2-1-yloxy-tris-pyrrolidinophosphonium hexafluorophosphate (0.031 g), compound (2a) (0.044 g), diisopropylethylamine (0.104 mL) and DMF (3 mL) were stirred together for 18 h. After addition of trifluoroacetic acid (0.115 mL), and solvent removal in vacuo, the residue was purified by preparative reverse phase HPLC (20–30% MeCN gradient over 20 min, trifluoroacetic acid buffered) to afford Intermediate (13) (0.077 g).

LC/MS (Method B) MH$^+$/2 891.8; T$_{ret}$=8.23 min

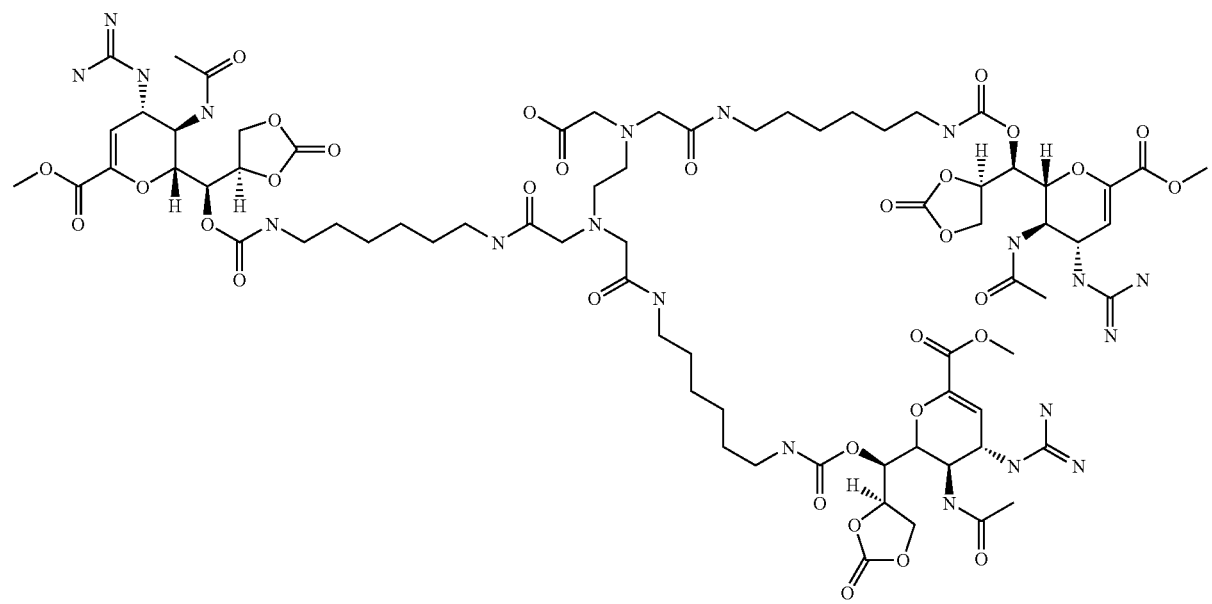

Intermeditate (13)

(1S)-1-{(2R,3R,4S)-3-(acetylamino)-4-{[amino(imino)methyl]amino}-6-[(methyloxy)carbonyl]-3,4-dihydro-2H-pyran-2-yl}-14,17-bis{2-[(6-{[({(S)-{(2R,3R,4S)-3-(acetylamino)-4-{[amino(imino)methyl]amino}-6-[(methyloxy)carbonyl]-3,4-dihydro-2H-pyran-2-yl}[(4R)-2-oxo-1,3-dioxolan-4-yl]methyl}oxy)carbonyl]amino}hexyl)amino]-2-oxoethyl}-3,12-dioxo-1-[(4R)-2-oxo-1,3-dioxolan-4-yl]-2-oxa-4,11,14,17-tetraazanonadecan-19-oic acid Intermediate (13) (0.005 g), water (1 mL), methanol (1 mL) and diisopropylethylamine (0.2 mL) were mixed vigourously together for 2 h after which the volatiles were blown off with a stream of nitrogen. Purification of the residue by reverse phase preparative HPLC (0–50% MeCN over 25 min) afforded Compound (14) (0.0031 g).

Compound (14)

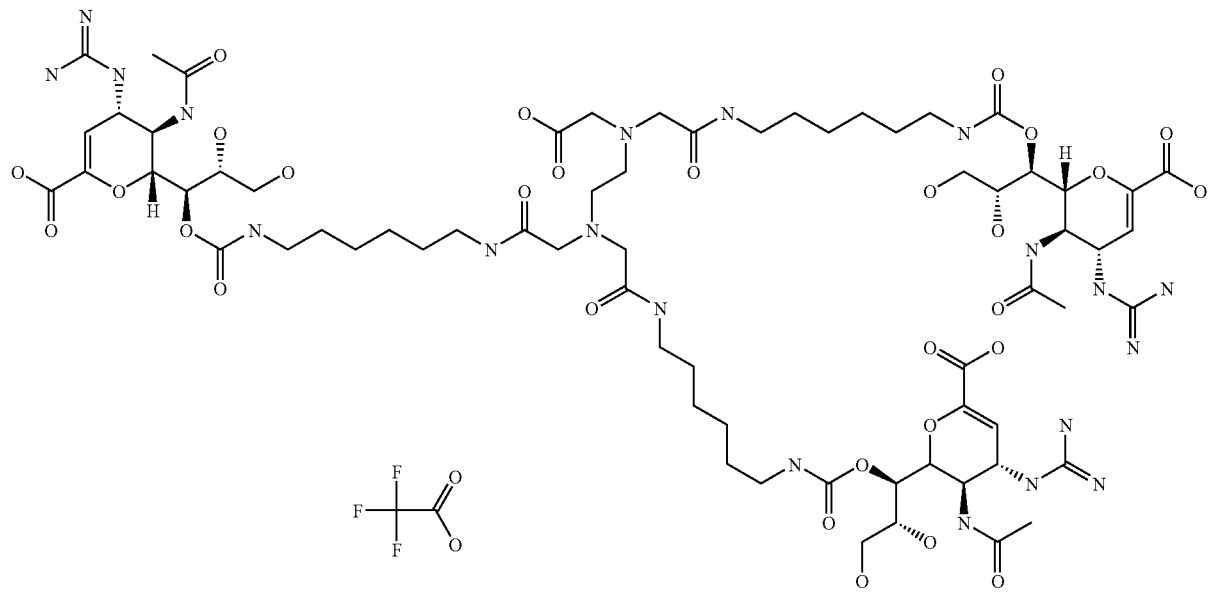

(19R,20R)-19-((2R,3R,4S)-3-(acetylamino)-4-{[amino(imino)methyl]amino}-6-carboxy-3,4-dihydro-2H-pyran-2-yl)-3,6-bis[2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}amino)-2-oxoethyl]-20,21-dihydroxy-8,17-dioxo-18-oxa-3,6,9,16-tetraazahenicosan-1-oic acid tris(trifluoroacetate)

LC/MS (Method B) MH+/2 831; $T_{ret}$=7.41 min

EXAMPLE 5

Compound (18) and (19)

Intermediate (15)
Intermediate (15)

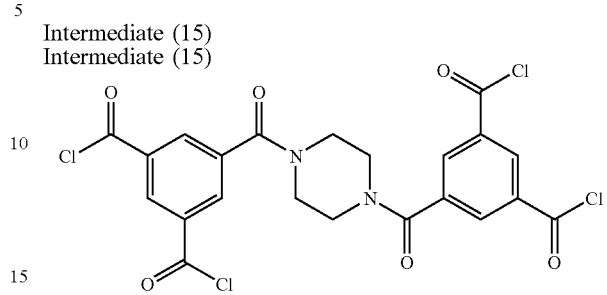

5-[(4-{[3,5-bis(chlorocarbonyl)phenyl]carbonyl}piperazin-1-yl)carbonyl]benzene-1,3-dicarbonyl dichloride At 5° C., to 3,5-diethylcarboxybenzoic acid (1.55 g) was added dichloromethane (100 mL), dimethylformamide (0.1 mL) and oxalyl chloride (0.5 mL). After 3 h at room temperature, the volatiles were removed in vacuo and the residue azeotroped with toluene.

To this residue was added dichloromethane (100 mL), piperazine (0.251 g) and triethylamine (0.89 mL). After stirring at room temperature for 3 days, the mixture was washed with 2M hydrochloric acid (2×100 mL), 2N sodium carbonate (2×150 mL), brine (50 mL) and dried (MgSO4). Concentration in vacuo afforded a white solid (0.82 g).

To this white solid was added methanol (20 mL), water (7 mL), tetrahydrofuran (20 mL) and lithium hydroxide (0.145 g). After 2 days at room temperature, the organic solvents were removed in vacuo and 2M hydrochloric acid added to the residue to pH4. The white precipitate that formed was filtered off, washed with water and dried to afford a white solid (0.626 g).

A portion of this white solid (0.200 g) was azeotroped with toluene (2×50 mL) and then suspended in dichloromethane (100 mL). Oxalyl chloride (0.185 mL) and dimthylformamide (2 drops) were then added. After 1 h, further oxalyl chloride (0.185 mL) and dimethylformamide (1 drop) was added. After 30 min, the solvents were removed in vacuo and the residue azeotroped with toluene (2×20 mL) to afford Intermediate (15) as a pale cream solid (0.214 g) which was used without further purification or analysis.

Intermediates (16) and (17)

Intermediate (16)

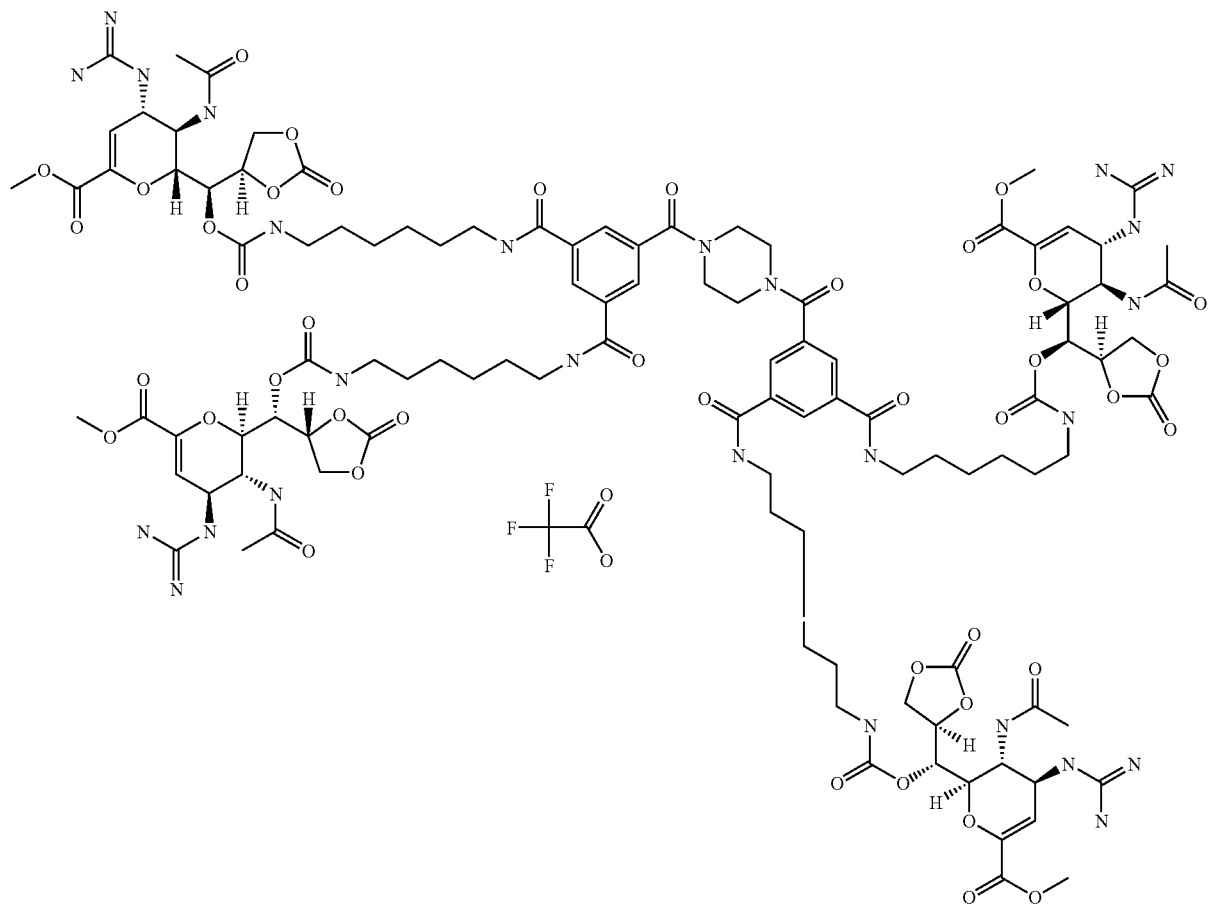

5-{[4-({3,5-bis[(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}aminocarbonyl]phenyl}yl}carbonyl)piperazin-1-yl]carbonyl}-N,N'-di(2-({6-[({[(1R,2R)-1-((2R,3R,4S)-3-(acetylamino)-4-{(amino(imino)methyl]amino}-6-carboxy-3,4-dihydro-2H-pyran-2-yl)-2,3-dihydroxypropyl]oxy}carbonyl)amino]hexyl}aminocarbonyl)benzene-1,3-dicarboxamide tetrakis (trifluoroacetate)

Intermediate (17)

3-{[4-((3,5-bis[(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy)carbonyl)amino]hexyl})amino)carbonyl]phenyl}carbonyl)piperazin-1-yl]carbonyl}-5-[(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}amino)carbonyl]benzoic acid tris(trifluoroacetate).

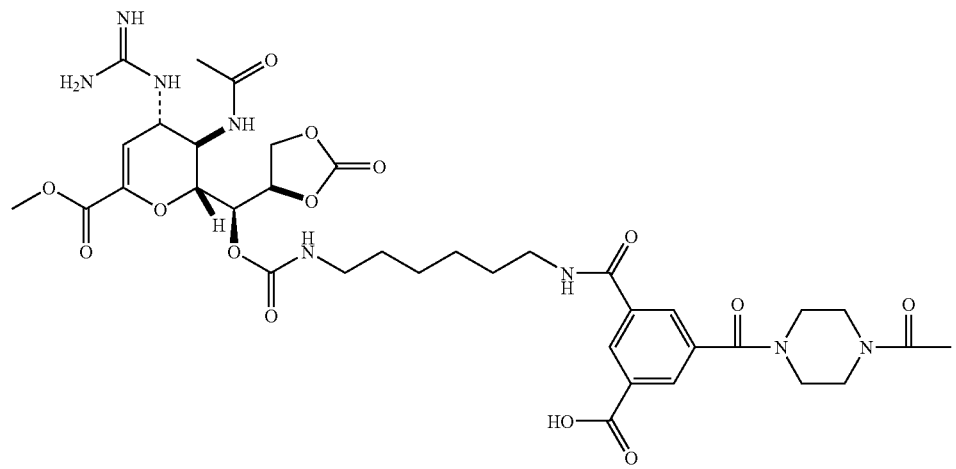

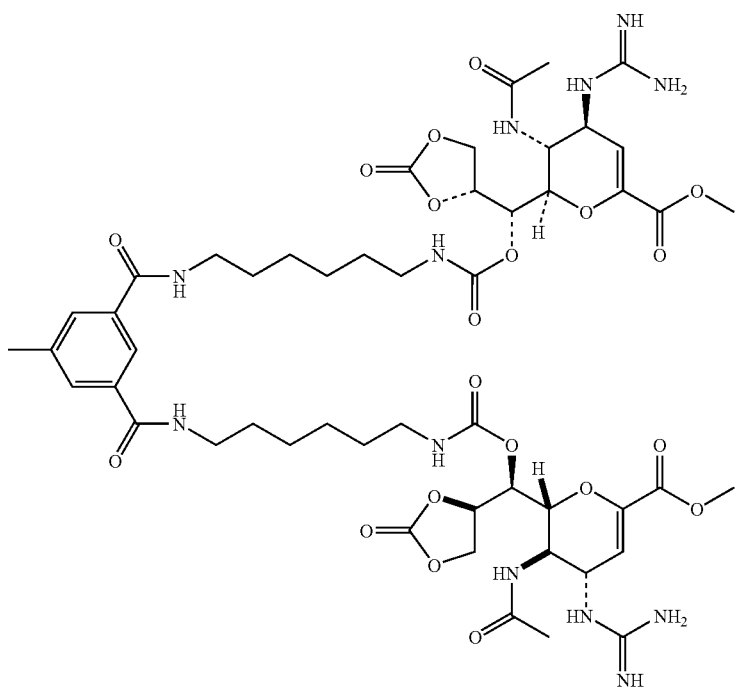

Compound (2a) (0.100 g) was azeotroped with toluene (15 mL). The residue was then suspended in dichloromethane (2 mL) and acetonitrile (2 mL) and to this added diisopropylethylamine (0.47 mL) and Intermediate (15) (0.015 g). After 3 h, the solvents were removed in vacuo and the residue purified by reverse phase HPLC (20–30% MeCN over 45 min) to afford Intermediate (16) (0.0125 g) and Intermediate (17) (0.0039 g).

Intermediate (16)

LC/MS (Method B) MH$^+$/2 1228; T$_{ret}$=8.79 min

Intermediate (17)

LC/MS (Method B) MH$^+$/2 980; T$_{ret}$=9.01 min

Compound (18)

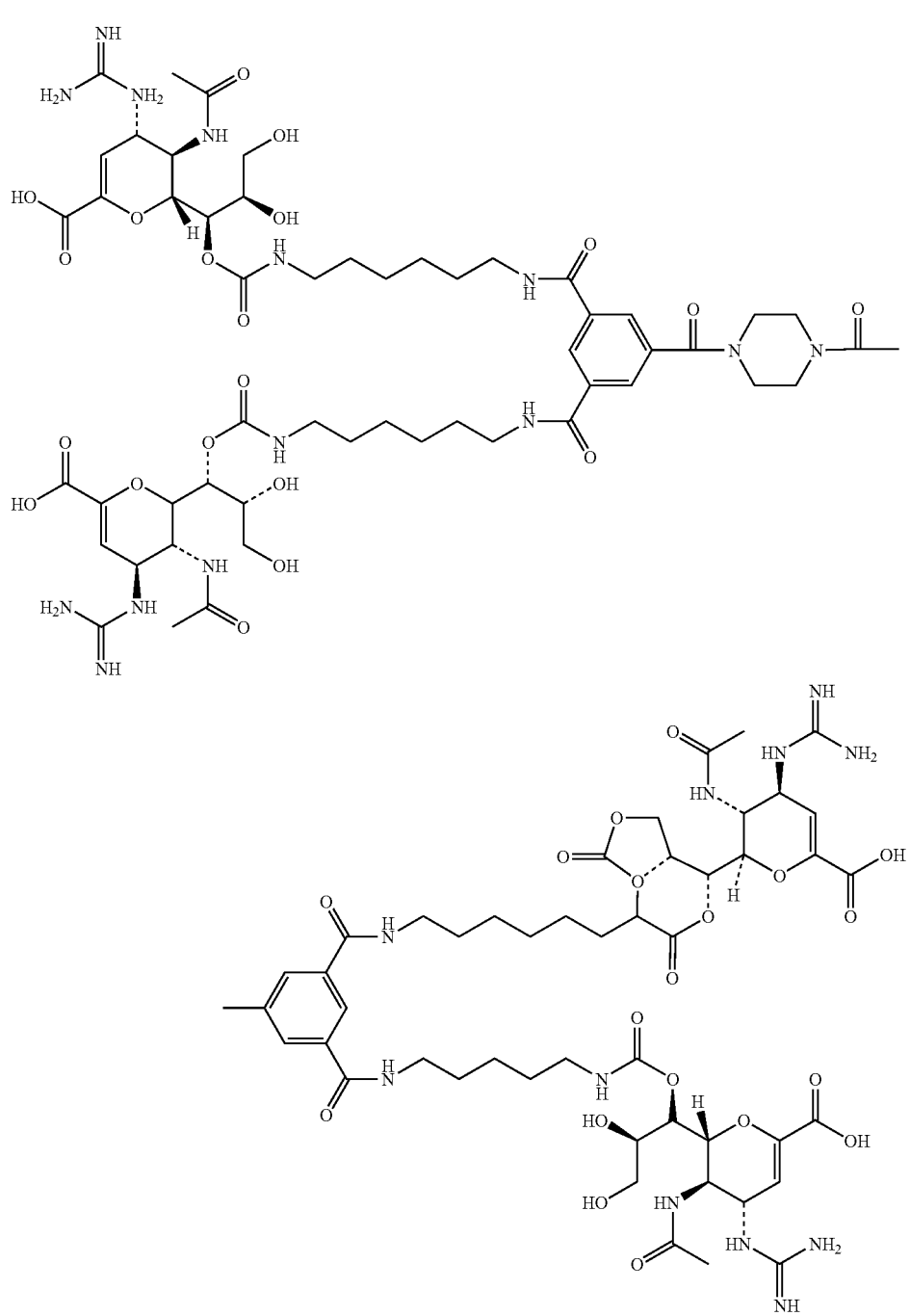

Compound (18)

5-{[4-({3,5-bis[(2-({6-[({[(1R,2R)-1-((2R,3R,4S)-3-(acetylamino)-4-{[(amino(imino)methyl]amino}-6-carboxy-3,4-dihydro-2H-pyran-2-yl)-2,3-dihydroxypropyl]oxy}carbonyl)amino]hexyl}amino)carbonyl]phenyl}carbonyl)piperazin-1-yl]carbonyl}-N,N'-bis(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}amino)benzene-1,3-dicarboxamide tetrakis (trifluoroacetate)

Intermediate (16) (0.0079 g), methanol (1 mL), water (1 mL) and triethylamine (0.2 mL) were mixed for 2 h. After removal of the volatiles, the aqueous residue was acidified with trifluoacetic acid to pH 2) and then purified by reverse phase HPLC (20–40% MeCN over 20 min) to afford Compound (18) (0.0035 g).

LC/MS (Method B) MH$^+$/2 1149; T$_{ret}$=8.24 min

Compound (19)

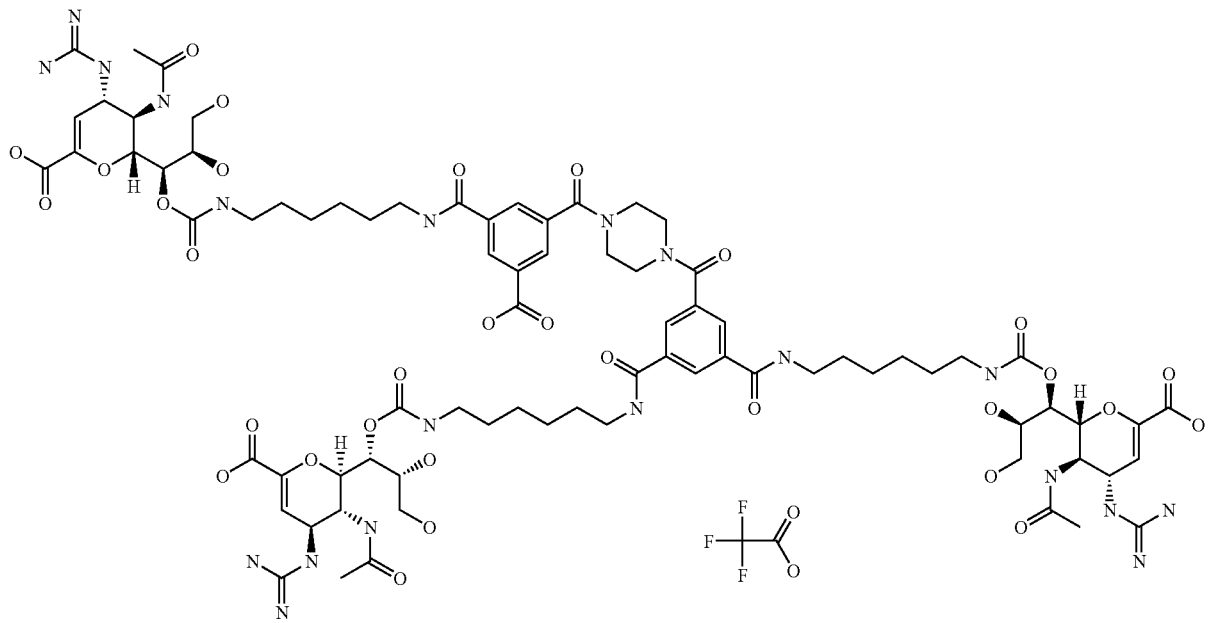

Compound (19)

3-{[4-(3,5-bis[(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}amino)carbonyl]phenyl}carbonyl)piperazin-1-yl]carbonyl}-5-[(2-({6-[({[(1R,2R)-1-((2R,3R,4S)-3-(acetylamino)-4-{[amino(imino)methyl]amino}-6-carboxy-3,4-dihydro-2H-pyran-2-yl)-2,3-dihydroxypropyl]oxy}carbonyl)amino]hexyl}amino)carbonyl]benzoic acid tris(trifluoroacetate)

Intermediate (17) (0.0033 g), methanol (1 mL), water (1 mL) and triethylamine (0.2 mL) were mixed for 2 h. After removal of the volatiles, the aqueous residue was acidified with trifluoacetic acid to pH 2) and then purified by reverse phase HPLC (20–40% MeCN over 20 min) to afford Compound (19) (0.0019).

LC/MS (Method B) MH+/2 920; $T_{ret}$=8.24 min

EXAMPLE 6

Preparation of the Tetramer (20) and the Trimer (21) from Coupling of 1,2,4,5-Benzenetetracarboxylic Acid and Compound (2a)

The synthesis of Compounds (20) and (21) was carried out following essentially the same method as for Compound (4) and as described in Example 2, except that 1,2,4,5-benzenetetracarboxylic acid was used instead of trimesic acid. The compounds were separated by HPLC and characterised by $^1$H NMR and Mass Spectrometry.

Compound (20)

$^1$H nmr (CD$_3$OD): δ 1.37 (br, 16H); 1.47 (br, 8H); 1.58 (br, 8H); 1.91 (s, 12H); 3.00 (m, 8H); 3.31 (m, 8H); 3.46 (dd, 4H); 3.62 (dd, 4H); 3.99 dd, 4H); 4.14 (dd, 4H); 4.48 (dd, 4H); 4.63 (dd, 4H); 4.93 (dd, 4H); 5.84 (d, 4H); 7.65 (s, 2H). MS (MW 2080.16): 1041 (M+2H)$^{2+}$, 694 (M+3H)$^{3+}$, 521 (M+4H)$^{4+}$ Compound (21)

$^1$H nmr (D$_2$O): δ 1.37 (br, 12H); 1.51 (br, 6H); 1.63 (br, 6H); 1.93 (br, 9H); 3.05 (m, 6H); 3.32 (m, 6H); 3.50 (dd, 3H); 3.75 (dd, 3H); 3.98 (m, 3H); 4.18 (dd, 3H); 4.37 (dd, 3H); 4.53 (dd, 3H); 5.01 (dd, 3H); 5.87 (d, 3H); 7.52 (s, 1H); 8.08 (s, 1H). MS (MW 1623.66): 1083 (2M+3H)$^{3+}$, 813 (M+3H)$^{2+}$, 542 (M+3H)$^{3+}$

EXAMPLE 7

Preparation of the Trimer (22) from Coupling of 1,2,4-Benzenetricarboxylic Acid and Compound (2a)

The synthesis of Compound (22) was carried out following essentially the same method as for Compound (4) and as described in Example 2, except that 1,2,4-benzenetricarboxylic acid was used instead of trimesic acid.

(MW 1578): 1579 (M+H)$^+$, 1053 (2M+3H)$^{3+}$, 790 (M+2H)$^{2+}$

EXAMPLE 8

Preparation of the Tetramer (23) from Coupling of 4-t-Butylcalix[4]arene-O-tetraacetic Acid and Compound (2a)

The synthesis of Compound (23) was carried out following essentially the same method as for Compound (4) and as described in Example 2, except that 4-t-Butylcalix[4]arene-O-tetraacetic acid was used instead of trimesic acid.

$^1$H nmr (CD$_3$OD): δ (ppm) μ 1.12 (s, 28H); 1.21 (s, 8H) 1.30–1.65 (br, 32H); 1.95 (s, 12H); 3.0 (m, 8H); 3.2–3.4 (m, 16H); 3.51 (dd, 4H); 3.63 (dd, 4H); 4.00 (m, 4H); 4.22 (dd, 4H); 4.37 (dd, 4H); 4.52 (s, 8H); 4.54 (dd, 4H); 4.97 (dd, 4H); 5.85 (d, 4H); 6.95 (br, 6.2H); 7.41 (s, 1.8H). MS (MW 2704): 1354 (M+4H)$^{2+}$, 902 (M+3H)$^{3+}$, 677 (M+4H)$^{4+}$

EXAMPLE 9

Preparation of the Trimer (24) from Coupling of 1,2,3-Benzenetricarboxylic Acid and Compound (2a)

The synthesis of Compound (24) was carried out following essentially the same method as for Compound (4) and as described in Example 2, except that 1,2,3-benzenetricarboxylic acid was used instead of trimesic acid.
MS (MW 1578): 790 (M+3H)$^{2+}$, 527 (M+3H)$^{3+}$

EXAMPLE 10

Preparation of the Trimer (25) from Coupling of Tricarballylic Acid and Compound (2a)

The synthesis of Compound (25) was carried out following essentially the same method as for Compound (4) and as described in Example 2, except that tricarballylic acid (1,2,3-propanetricarboxylic acid) was used instead of trimesic acid.
$^1$H nmr (D$_2$O): δ 1.28 (br, 12H); 1.45 (br, 12H); 1.96 (s, 9H); 2.40 (dd, 4H); 2.98–3.18 (m, 13H); 3.50 (dd, 3H); 3.65 (dd, 3H); 4.02 (dd, 3H); 4.16 (dd, 3H); 4.43 (dd, 3H); 4.57 (dd, 3H); 4.93 (dd, 3H); 5.98 (d, 3H). MS (MW 1544): 1546 (M+2H)$^+$, 773 (M+2H)$^{2+}$, 516 (M+3H)$^{3+}$

EXAMPLE 11

Preparation of the Trimer (26) from Coupling of 1,3,5-Cyclohexanetricarboxylic Acid (cis) and Compound (2a)

The synthesis of Compound (26) was carried out following essentially the same method as for Compound (4) as described in Example 2, except that 1,3,5-cyclohexanetricarboxylic acid (cis, Sigma-Aldrich) was used instead of trimesic acid.
$^1$H nmr (D$_2$O): δ 1.32 (br, 12H); 1.45–1.60 (br, 15H); 1.93 (d, 3H); 1.99 (s, 9H); 2.42 (dd, 3H); 3.08 (m, 6H); 3.18 (m, 6H); 3.53 (dd, 3H); 3.68 (dd, 3H); 4.05 (ddd, 3H); 4.18 (dd, 3H); 4.47 (dd, 3H); 4.59 (dd, 3H); 4.99 (dd, 3H); 6.07 (d, 3H). MS (MW 1585): 1586 (M+H)$^+$, 1057 (2M+3H)$^{3+}$, 793 (M+2H)$^{2+}$, 529 (M+3H)$^{3+}$

EXAMPLE 12

Preparation of the Tetramer (27) from Coupling of 1,2,3,4-Tetrahydrofuran-tetracarboxylic Acid and Compound (2a)

The synthesis of Compound (27) was carried out following essentially the same method as for Compound (4) and as described in Example 2, except that 1,2,3,4-tetrahydrofuran-tetracarboxylic acid was used instead of trimesic acid.
$^1$H nmr (D$_2$O): δ 1.27 (br, 16H); 1.43 (br, 16H); 1.93 (s, 12H); 2.92–3.40 (m, 18H); 3.45 (dd, 4H); 3.62 (dd, 4H); 4.00 (m, 4H); 4.11 (dd, 4H); 4.40 (dd, 4H); 4.52 (dd, 4H) 4.62 (d, 2H); 4.72 (d, 2H); 4.90 (dd, 4H); 5.89 (d, 4H). MS (MW 2072): 1038 (M+4H)$^{2+}$, 692 (M+4H)$^{3+}$

EXAMPLE 13

Preparation of the Tetramer (28) from Coupling of 1,2,3,4-Cyclobutane-tetracarboxylic Acid and Compound (2a)

The synthesis of Compound (28) was carried out following essentially the same method as for Compound (4) and as described in Example 2, except that 1,2,3,4-cyclobutane-tetracarboxylic acid (Sigma-Aldrich) was used instead of trimesic acid.
$^1$H nmr (D$_2$O): δ 1.23 (br, 16H); 1.43 (br, 16H); 1.93 (s, 12H); 2.95–3.20 (m, 16H); 3.47 (dd, 4H); 3.55–3.70 (m, 8H); 4.01 (m, 4H); 4.10 (dd, 4H); 4.40 (dd, 4H); 4.50 (dd, 4H); 4.89 (dd, 4H); 5.85 (d, 4H). MS (MW 2056): 1030 (M+4H)$^{4+}$, 686 (M+2H)$^{3+}$

EXAMPLE 14

Preparation of the Trimer (29) from Coupling of 1,3,5-Benzenetricarboxylic Acid and Compound (30)

The synthesis of Compound (29) was carried out following essentially the same method as for Compound (4) and as described in Example 2, except that the lysine derivative (30) was used instead of compound (2a).

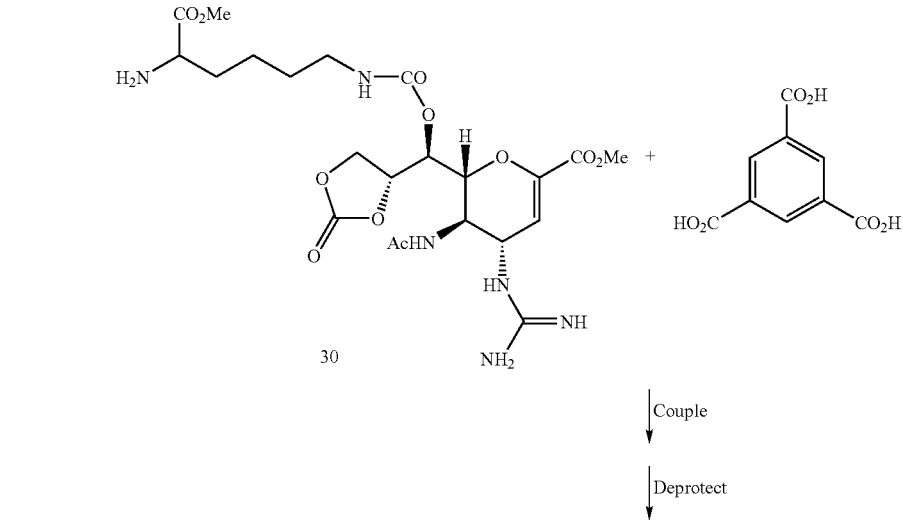

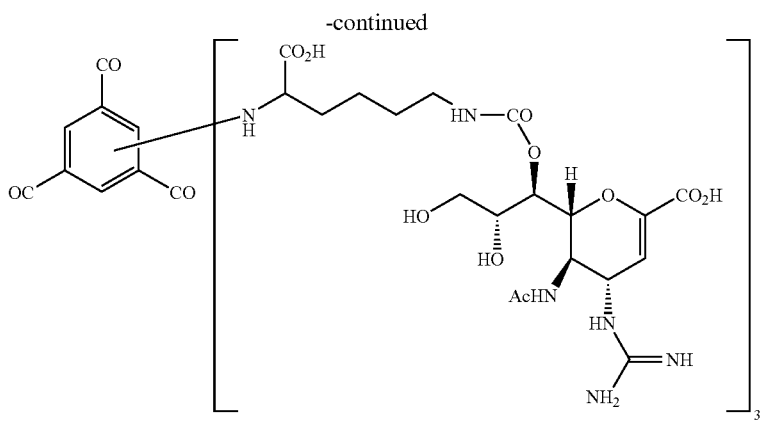

29

$^1$H nmr (D$_2$O): δ 1.4–1.6 (br, 12H); 1.80–1.98 (br, 15H); 3.05 (m, 6H); 3.44 (dd, 3H); 3.60 (dd, 3H); 3.98 (m, 3H); 4.02 (dd, 3H); 4.37 (dd, 3H); 4.46 (m, 6H); 4.87 (dd, 3H); 5.65 (d, 3H); 8.28 (br, 3H). MS (MW 1668): 835 (M+2H)$^{2+}$, 557 (M+3H)$^{3+}$

EXAMPLE 15

Preparation of the Trimer (31) from Coupling of Citric Acid and Compound (2a)

The synthesis of Compound (31) was carried out following essentially the same method as for Compound (4) as described in Example 2, except that citric acid was used instead of trimesic acid.

$^1$H nmr (D$_2$O): δ 1.26 (br, 12H); 1.38 (br, 12H); 1.93 (s, 9H); 2.50 (d, 2H); 2.69 (dd, 2H); 2.95–3.20 (m, 12H); 3.47 (dd, 3H); 3.65 (dd, 3H); 3.99 (m, 3H); 4.14 (dd, 3H); 4.42 (dd, 3H); 4.52 (dd, 3H); 4.91 (dd, 3H); 5.96 (d, 3H). MS (MW 1560): 781 (M+2H)$^{2+}$, 521 (M+3H)$^{3+}$

EXAMPLE 16

Preparation of the Trimer (32) from Coupling of 1,3,5-Benzenetricarboxylic Acid and Compound (33)

The synthesis of Compound (32) was carried out following essentially the same method as for Compound (4) and as described in Example 2, except that the 1,3-propanediamine derivative (33) was used instead of compound (2a).

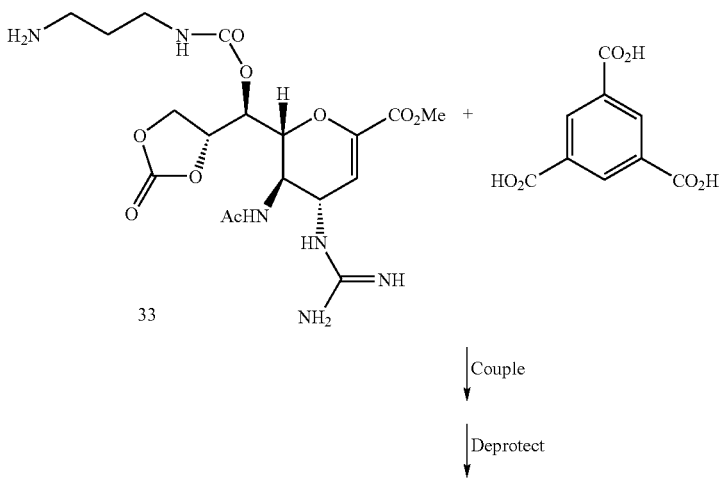

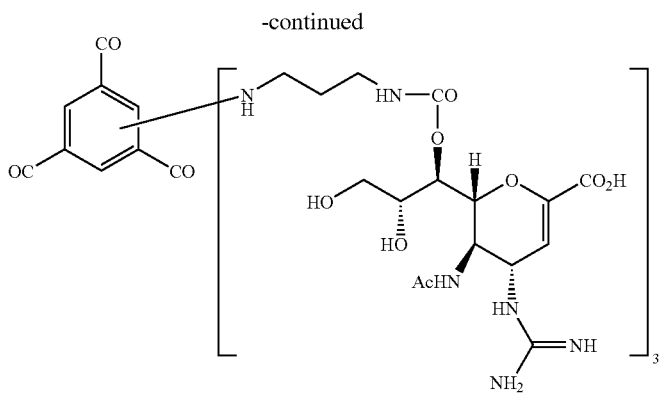

32

$^1$H nmr (D$_2$O): δ 1.80 (t, 6H); 1.93 (s, 9H); 3.19 (t, 6H) 3.40–3.50 (m, 9H); 3.64 (dd, 3H); 4.0 (m, 3H); 4.09 (t, 3H); 4.37 (dd, 3H); 4.47 (dd, 3H); 4.94 (dd, 3H); 5.80 (d, 3H); 8.24 (s, 3H). MS (MW 1452): 727 (M+2H)$^{2+}$, 485 (M+3H)$^{3+}$

EXAMPLE 17

Determination of the Binding of the Compounds of the Invention to Influenza Virus Neuraminidase (NA)

An influenza A and an influenza B virus are used to test the ability of the compounds to bind to whole virus influenza neuraminidase. The neuraminidase assay is carried out essentially following the procedure described by Potier et al., *Anal. Biochem.*, 1979 94, 287.

EXAMPLE 18

Assessment of the Antiviral Activity of the Compounds of the Invention Using an Influenza Plaque Assay Plaque assays are performed essentially as described by Hayden et al. (Antimicrob. Agents Chemother., 1980, 17, 865). MDCK cell monolayers are infected with approximately 100 plaque forming units of influenza virus. After virus adsorption, cells are overlaid with agarose containing half log dilutions of the test compound using concentrations ranging for example from 0.1 µg/ml down to 0.0003 µg/ml. The plates are incubated for 4 days and then fixed with formalin overnight. After removal of the agarose layer the plates are stained with neutral red to allow visualisation of plaques. The plates are evaluated for inhibition of plaque number and the EC$_{50}$ determined for each compound.

| Compound Number | EC$_{50}$ on Influenza A/WSN/33 |
| --- | --- |
| (A) Zanamivir | 22.7 ng/ml |
| 4 | <0.01 ng/ml |
| 20 | <0.01 ng/ml |
| 22 | <0.01 ng/ml |

| Compound Number | EC$_{50}$ on Influenza A/Victoria/3/75 | EC$_{50}$ on Influenza B/Victoria/1/87 |
| --- | --- | --- |
| (A) Zanamivir | 3.5 ng/ml | 16 |
| 3 | 0.1 | 0.3 |
| 4 | 0.3 | 0.7 |
| 14 | — | 6.3 |
| 20 | 0.2 | 0.4 |

EXAMPLE 19

Activity of Compound Against Influenza Virus

The trimeric compound of Example 3 was tested for its ability to inhibit the replication of influenza A and influenza B virus, essentially following the standard method described in the literature (see for example Watanabe et al, J. Virological Methods, 1994 48 257). The assay was carried out using MDCK cells and three different influenza virus strains, two influenza A and one influenza B, and the results are shown in Table 1. The results are shown as IC$_{50}$, the minimum compound concentration which inhibits cytopathic effect by 50% [(µg/ml)], calculated by using a regression analysis program for semi-log curve fitting. The results show that the trimeric-compound (4) was much more active against all three influenza virus strains than the highly active compound Zanamivir (compound (A)). The therapeutic index for the compounds can be calculated by dividing the minimum cytotoxic drug concentration (MTC) by the ID$_{50}$.

| Compound | Virus strain | MW of compound | No of ZMV per molecule | IC$_{50}$ ng/ml | IC$_{50}$ nM | IC$_{50}$ nM per ZMV equiv |
| --- | --- | --- | --- | --- | --- | --- |
| Zanamivir (ZMV) | A/Sydney/5/97 | 332 | 1 | 25.78 | 77.65 | 77.65 |
| Compound (2) TFA$_2$ | A/Sydney/5/97 | 702 | 1 | 412.7 | 588 | 588 |
| Trimer Compound (4) | A/Sydney/5/97 | 1921 (TFA salt) | 3 | 0.782 | 0.40 | 1.20 |
| Zanamivir | B/Harbin/7/95 | 332 | 1 | 10.376 | 31.22 | 31.22 |

-continued

| Compound | Virus strain | MW of compound | No of ZMV per molecule | IC$_{50}$ ng/ml | IC$_{50}$ nM | IC$_{50}$ nM per ZMV equiv |
|---|---|---|---|---|---|---|
| Compound (2) TFA$_2$ | B/Harbin/ 7/95 | 702 | 1 | 181.8 | 258.9 | 258.9 |
| Trimer Compound (4) | B/Harbin/ 7/95 | 1921 (TFA salt) | 3 | 0.875 | 0.46 | 1.37 |
| Zanamivir | A/Victoria/ 3/75 | 332 | 1 | 24.57 | 73.93 | 73.93 |
| Compound (2) TFA$_2$ | A/Victoria/ 3/75 | 702 | 1 | 37.0 | 52.7 | 52.7 |
| Trimer Compound (4)) | A/Victoria/ 3/75 | 1921 (TFA salt) | 3 | 0.71 | 0.37 | 1.21 |

Following the same protocol as above, the compounds of the invention gave the CPE results summarised in the Table below.

| Compound Number | EC$_{50}$ on Influenza A/Sydney/5/97 | EC$_{50}$ on Influenza B/Harbin/7/95 |
|---|---|---|
| (A) Zanamivir | 32.674 | 14.187 |
| 4 | 0.822 | 1.065 |
| 20 | 0.7 | 1.115 |
| 21 | 0.73 | 1.068 |
| 22 | 0.992 | 1.051 |
| 23 | 27.714 | 9.263 |
| 24 | 0.62 | 2.312 |
| 25 | 0.4 | 0.809 |
| 26 | 0.3 | 0.438 |
| 27 | 0.316 | 1.472 |
| 28 | 0.358 | 1.631 |
| 29 | 0.089 | 0.882 |
| 31 | 0.159 | 2.475 |
| 32 | 0.163 | 1.018 |

EXAMPLE 20

Assessment of Long Duration of Action

Rodents are anaesthetised and dosed with compound of interest by the intra-tracheal route at a dose volume of 0.8 ml/kg. The rodent is then held in the vertical position until full recovery is achieved. At different time points, for example, 2, 8, 24 and 48 hours post-dose, levels of compound in the lung tissue are assessed by analytical methods. Any analytical method suitable for detection of this type of compound may-be used. The time at which levels of compound fall below the sensitivity of the analytical techniques identified will determine the residency time of the compound in lung tissue.

The multimeric Compounds No 3, 4 and 20 of the invention were tested in parallel with Zanamivir [Compound (A)] using a dose of 0.4 mg/kg for each compound and assessing the level of compound in the lung tissue after 48 and 168 hours, using LC-MS/MS. The analysis showed that Compounds 3, 4 and 20 were retained in the lung at much higher concentrations than the monomer Zanamivir (A).

EXAMPLE 21

Alternative Assessment of Long Duration of Action and Efficacy

The protocol for infecting mice has been described previously (1, 2, 3, 4). Mildly anaesthetised mice are inoculated into the external nares with influenza virus. Treatment procedure and regimen. A single dose of compound is administered at a defined time point up to 10 days prior to infection, preferably 4–7 days prior to infection, or following infection, preferably immediately following infection and up to 48 hours post infection. In most experiments, a non-lethal strain of influenza is used, and efficacy is assessed by reductions in lung virus titre. For mice given compound prior to infection, lungs are removed post infection either on a single day, or on days following infection, preferably days 1–4 post infection. Homogenised lung samples are assayed for virus using established methods, and the titres of viral load estimated and compared to titres of virus in lungs of untreated mice.

In those experiments where a mouse-adapted lethal strain of influenza is used, efficacy is assessed by an increase in survival rate and/or numbers of survivors, as compared to untreated mice.

(a) Using Influenza A/Victoria/3/75 and with lungs harvested 3 days post infection

| Compound No | Compound Dose | Number of mice in group | Mean Virus Titre ($logTCID_{50}$/ml) | Number of virus free mice | % Effectiveness |
|---|---|---|---|---|---|
| Control | 0 | 8 | 5.3/5.4 | 0 | — |
| (A) | 0.2 mg/kg | 7 | 5.5 | 0 | −43.4 |
| 3 | 0.2 mg/kg | 8 | 4.0 | 4 | 59 |
| 4 | 0.2 mg/kg | 8 | 3.7 | 3 | 95.2 |
| 20 | 0.2 mg/kg | 8 | 3.9 | 2 | 87.2 |
| 22 | 0.2 mg/kg | 7 | 3.8 | 3 | 89.9 |
| 23 | 0.2 mg/kg | 8 | 4.7 | 0 | 78.2 |
| 25 | 0.2 mg/kg | 8 | — | — | 93 |
| 28 | 0.2 mg/kg | 8 | — | — | 95 |

(b) Using Influenza A/Singapore/1/57 and with lungs harvested 1 day post infection

| Compound No | Compound Dose (mg/kg) | Number of mice in group | Mean Virus Titre ($logTCID_{50}$/ml) | Number of virus free mice | Effectiveness |
|---|---|---|---|---|---|
| Control | 0 | 10 | 5.78–6.05 | 0 | — |
| (A) | 5 | 10 | 4.58 | 1 | 93.69 |
| | 1 | 10 | 5.18 | 0 | 74.88 |
| | 0.2 | 10 | 5.60 | 0 | 33.17 |
| 3 | 1 | 10 | 3.78 | 1 | 99.47 |
| | 0.1 | 10 | 4.70 | 0 | 95.53 |
| | 0.01 | 10 | 5.55 | 0 | 68.38 |
| 4 | 1 | 9 | 4.13 | 0 | 98.79 |
| | 0.1 | 10 | 4.63 | 1 | 96.24 |
| | 0.01 | 10 | 5.53 | 0 | 70.15 |
| 20 | 1 | 10 | 2.30 | 9 | 99.68 |
| | 0.1 | 10 | 4.20 | 0 | 74.88 |
| 21 | 1 | 10 | 3.63 | 0 | 93.32 |
| | 0.1 | 9 | 4.47 | 0 | 53.58 |
| 22 | 1 | 10 | 2.68 | 7 | 99.25 |
| | 0.1 | 10 | 4.23 | 0 | 73.39 |
| 24 | 1 | 10 | 3.48 | 2 | 98.98 |
| | 0.1 | 10 | 4.98 | 0 | 67.77 |

(c) Using Influenza A/Victoria/3/75 and with lungs harvested 1 day post infection

| Compound No | Compound Dose (mg/kg) | Number of mice in group | Mean Virus Titre (logTCID$_{50}$/ml) | Number of virus free mice | Effectiveness |
|---|---|---|---|---|---|
| Control | 0 | 10 | 4.75–5.11 | 0 | — |
| (A) | 1 | 10 | 4.45 | 0 | 81.76 |
| 25 | 1 | 10 | 3.35 | 5 | 98.24 |
|  | 0.1 | 10 | 4.60 | 1 | 68.78 |
| 26 | 1 | 10 | 2.98 | 5 | 98.32 |
|  | 0.1 | 10 | 3.50 | 3 | 94.38 |
| 31 | 1 | 10 | 3.05 | 5 | 99.11 |
|  | 0.1 | 10 | 4.25 | 0 | 85.88 |

Ryan, D. M., J. Ticehurst, M. H. Dempsey, and C. R. Penn, 1994. Inhibition of influenza virus replication in mice by GG167 (4-guanidino-2,4-dideoxy-2,3-dehydro-N-acetylneuraminic acid) is consistent with extracellular activity of viral neuraminidase (sialidase). Antimicrob. Agents and Chemother. 38 (10):2270–2275.

von Itzstein M., W.-Y. Wu, G. B. Kok, M. S. Pegg, J. C. Dyason, B. Jin, T. V. Phan, M. L. Smythe, H. F. White, S. W. Oliver, P. M. Colman, J. N. Varghese, D. M. Ryan, J. M. Woods, R. C. Bethell, V. J. Hotham, J. M. Cameron, and C. R. Penn. 1993. Rational design of potent sialidase-based inhibitors of influenza virus replication. Nature (London) 363: 418–423

Woods, J. M. R. C. Bethell, J. A. V. Coates, N. Healey, S. A. Hiscox, B. A. Pearson, D. M. Ryan, J. Ticehurst, J. Tilling, S, A. Walcott, and C. R. Penn. 1993. 4-Guanidino-2,4-dideoxy-2,3-dehydro-N-acetylneuraminic acid is a highly effective inhibitor both of the sialidase (neuraminidase) and of growth of a wide range of influenza A and B viruses in vitro. Antimicrob. Agents Chemother. 37: 1473–1479

The assay methods described in Examples 19 to 21 are well known in the art and are generally accepted as predictive of efficacy in humans.

Robert J Fenton, Peter J Morley, Ian J Owens, David Gower, Simon Parry, Lee Crossman And Tony Wong (1999). Chemoprophylaxis of influenza A virus infections, with single doses of zanamivir, demonstrates that zanamivir is cleared slowly from the respiratory tract. Antimicrob. Agents and Chemother. 43, 11, 2642–2647

EXAMPLE 22

Powder Inhalation Formulation

| Active Ingredient. | 5 mg |
|---|---|
| Carrier e.g. lactose | 20 mg |

The active ingredient and the carrier are mixed together in a tumbling mixer.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The application of which this description and claims forms part may be used as a basis for priority in respect of any subsequent application. The claims of such subsequent application may be directed to any feature or combination of features described herein.

The invention claimed is:

1. A compound according to the formula (I):

(I)

in which:

X is O or $CH_2$;

R is an azido group, a hydroxy group, an optionally substituted guanidino group, an optionally substituted amino group, an optionally substituted amidine, or an optionally substituted imidate;

$R^2$ is $COCR^3{}_3$ or $SO_2CR^3{}_3$;

$R^3$ is independently selected from H, F, Cl, Br, I and $C_{1-6}$alkyl;

n is an integer of from 2 to 128;

Y is —O, —O(C=O), —$NR^4$, —$NR^4CO$, —O(C=O)$NR^4$, —O(C=S)$NR^4$, —$NR^4(C=O)O$, —$NR^4(C=S)O$, —$NR^4(C=O)NR^4$, —$NR^4(C=S)NR^4$, —$NR^4SO$, —$NR^4SO_2$, —$NR^4SONR^4$, or —$NR^4SO_2NR^4$ in which $R^4$ is H or $C_{1-6}$alkyl;

CG is a core group selected from an optionally substituted cycloalkyl, straight or branched group or a combination thereof having from 1 to 200 atoms in its backbone, in which the backbone atoms are selected from C, N, O and S; and L is a linking group of from 0 to 20 backbone atoms, in which the backbone and terminal atoms are selected from C, N, O and S;

or a pharmaceutically acceptable derivative, pharmaceutically acceptable salt, geometric isomer or stereoisomer thereof.

2. A compound according to claim 1, in which

X is O;

R is an optionally substituted amino or guanidino group;

$R^3$ is H, F or $C_{1-6}$alkyl;

n is an integer from 2 to 7;

Y is —O or —O(C=O)$NR^4$, in which $R^4$ is H and the group is bonded to the linking group L through the N atom; and L is a linking group of from 1 to 15 backbone atoms.

3. A compound according to claim 2, in which:

R is an unsubstituted amino or guanidino group;

n is 2 or 3;

Y is —O(C=O)$NR^4$ in which $R^4$ is H and the group is bonded to the linking group L through the N atom; and L is —HN($CH_2$)p in which p is an integer from 2 to 10.

4. A compound according to claim 1 which is a 7-carbamate derivative.

5. A compound according to claim 4 in which:

R is guanidine;

$R^2$ is acetyl;

X is O;

Y is —O(C=O)NH; and n is 2 to 7.

6. A compound according to claim 1 in which CG is selected from one or more of optionally substituted straight or branched hydrocarbon chains optionally containing heteroatoms selected from N, O or S, polyamidoamines, polyethylenimines, polyalkyl and polyaryl ethers, polyamidoalcohols, calixarenes, polyaminoacids, polyethylene glycol units, alkylamidoalkanes, oligolactates, oligoglycolates, ethylenediamine tetraacetic acid (EDTA), aryl, and cycloalkyl.

7. A compound according to claim 6, in which CG is selected from one or more of optionally substituted straight or branched hydrocarbon groups optionally comprising heteroatoms selected from N, O and S, polyamidoamines, EDTA, polyethylene glycol units, calixarenes, aryl, and cycloalkyl.

8. A compound according to claim 6, in which CG is selected from one or more of optionally substituted straight or branched hydrocarbon groups, optionally comprising heteroatoms selected from N, O and S, EDTA, aryl, and cycloalkyl.

9. A compound according to claim 1, in which the core group CG, linking group L, and/or group Y are selected to impart longer-lasting lung residence properties to the compounds of formula (I).

10. A compound according to claim 1, in which CG is of the formula (II);

$$W-CO(CH_2)_m\phantom{xx}(CH_2)_mCO-W$$
$$N-(R^5)_x-N$$
$$W-CO(CH_2)_m\phantom{xx}(CH_2)_mCO-W$$
(II)

in which:
W is independently selected from OH, $N(R^4)_2$ or -L-Y—B, in which $R^4$ defined in claim 1;
x is an integer from 1 to 10;
m is an integer from 1 to 4;
$R^5$ is a cyclic group selected from aryl, or cyclic $C_{1-10}$ alkyl, or an optionally substituted $C_{1-10}$ alkyl, $C_{3-10}$ alkenyl or $C_{3-10}$ alkynyl where one or more of the C atoms in the chain can optionally be replaced by a heteroatom selected from N, O and S or a combination thereof;
L is as defined in claim 1;
Y is as defined in claim 1;
B is H or a compound of formula (B):

(B)

in which:
X is $CH_2$;
R and $R^2$ are as defined in claim 1;
with the provisos that:
B cannot be H when Y is —NH(C=O)O or —NH(C=S)O;
not more than one W can be OH or $N(R^4)_2$ and not more than one B can be H, and W cannot be OH or $N(R^4)_2$ when B is H;
or a pharmaceutically acceptable derivative thereof and/or isomer thereof.

11. A compound according to claim 1, which is of the formula (III);

(III)

in which:
CG, L, Y, X, R and $R^2$ are as defined in claim 1.

12. A compound according to claim 11, in which the molecular weight is about 1,000 to about 100,000.

13. A compound according to claim 12, in which the molecular weight is about 1,000 to about 10,000.

14. A compound according to claim 13, in which the molecular weight is about 1,000 to about 5,000.

15. A process for the preparation of a compound of formula (I) as defined in claim 1, which comprises coupling a compound of formula (IV):

(IV)

in which:
Y* is $CO_2H$, —COLG, NCO, -halide, —OH, —$NR^3COLG$, —OCOLG, —OCSLG, $SO_2LG$, $NR^3SO_2LG$, $NR^3CSLG$, epoxides, or Michael acceptors; and
LG is a leaving group or a protected derivative thereof; with a compound of formula (V):

(V)

in which:
Y** is $NHR^3$ or OH or an activated or protected derivative thereof optionally followed by de-protection if necessary.

16. A process for the preparation of a compound of formula (I) as defined in claim 1 which comprises reacting a compound of formula (VI):

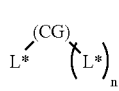
(VI)

in which:

L* is L-NHR³, L-OH, L-CO₂H, or a protected derivative thereof, with a compound of formula (VII):

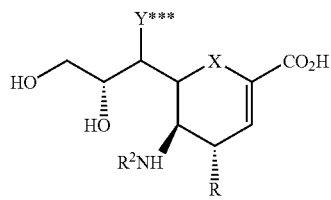
(VII)

in which:

Y*** is D-AG or halogen;

D is O or NR³;

AG is COLG, H, CSLG or SO₂LG; and

LG is a leaving group or a protected derivative thereof.

17. A process for the preparation of a compound of formula (II) as defined in claim 10 which comprises coupling a compound of general formula (VIII):

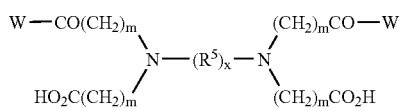
(VIII)

or a protected derivative thereof, with a compound of formula B-Y-L-H, or a protected derivative thereof, in which:

B, Y, and L are as defined in claim 10 and the atom in L bonded to H is a heteroatom;

optionally followed by deprotection if necessary.

18. A process for the preparation of a compound of formula (II) as defined in claim 10 which comprises coupling a compound of formula (V) as defined in claim 15 or a protected derivative thereof with a compound of formula (XI):

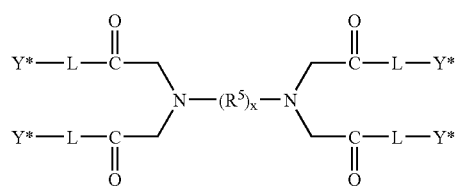
(XI)

in which:

Y* and L are as defined in claim 15 optionally followed by deprotection if necessary.

19. A process for the preparation of a compound of formula (II) as defined in claim 10 in which the terminal atom in L is nitrogen which comprises coupling a compound of formula (XII):

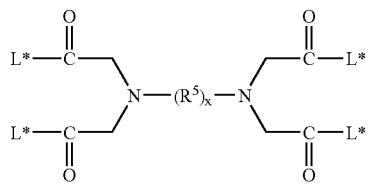
(XII)

or a protected derivative thereof, with a compound of formula (VII) as defined in claim 16, or a protected derivative thereof optionally followed by deprotection if necessary.

20. A process for the preparation of a compound of formula (II) as defined in claim 10 wherein R⁵ is an optionally substituted alkyl group which comprises a reaction of a compound of formula (XIII):

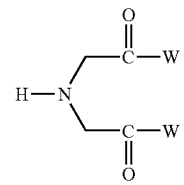
(XIII)

in which:

W is as defined in claim 10, or a protected derivative thereof, with an optionally substituted alkyl halide optionally followed by deprotection if necessary.

21. A pharmaceutical composition comprising a therapeutically effective amount of a compound of formula (I) of claim 1 or a pharmaceutically acceptable derivative thereof, together with one or more pharmaceutically acceptable carries.

22. A composition according to claim 21 further comprising at least one other or additional therapeutic and/or prophylactic ingredient.

23. A composition according to claim 22, in which the other therapeutic and/or prophylactic ingredient is an anti-infective agent.

24. A composition according to claim 23, in which the anti-infective agent is an anti-bacterial or anti-viral agent.

25. A composition according to claim 24, in which the anti-viral agent is a sialic acid analogue, amantadine, rimantadine and/or ribavirin.

26. An inhaler which contains a composition according to claim 21.

27. An inhaler according to claim 26 which is adapted for oral administration as a free-flow powder.

28. An inhaler according to claim 26 which is a metered dose aerosol inhaler.

29. A method for the treatment and/or prophylaxis of an orthomyxovirus infection which comprises the step of administration of an effective amount of a compound as defined in claim 1 to a subject in need thereof.

30. A method according to claim 29, in which the infection is caused by influenza A or B.

31. A method according to claim 29, in which the subject is a mammal.

32. A method according to claim 31, in which the mammal is a human.

33. A method according to claim 29, in which the amount of compound administered is in the range of from about 0.0001 to about 100 mg/kg of bodyweight per day.

34. A method according to claim 29, in which the compound is administered to the respiratory tract by inhalation, insufflation or intranasal administration or a combination thereof.

35. A method for the treatment of a paramyxovirus infection which comprises the step of administration of an effective amount of a compound as defined in claim 1 to a subject in need thereof.

36. A method according to claim 35, in which the subject is a mammal.

37. A method according to claim 36, in which the mammal is a human.

38. A method according to claim 35, in which the amount of compound administered is in the range of from about 0.0001 to about 100 mg/kg of bodyweight per day.

39. A method according to claim 35, in which the compound is administered to the respiratory tract by inhalation, insufflation or intranasal administration or a combination thereof.

* * * * *

UNITED STATES PATENT AND TRADEMARK OFFICE
CERTIFICATE OF CORRECTION

| | |
|---|---|
| PATENT NO. | : 7,205,333 B2 |
| APPLICATION NO. | : 10/363988 |
| DATED | : April 17, 2007 |
| INVENTOR(S) | : Wen-Yang Wu et al. |

It is certified that error appears in the above-identified patent and that said Letters Patent is hereby corrected as shown below:

IN THE SPECIFICATION

In Column 7, Line 45: Please delete "lp;.5plt will be appreciated" and replace with -- It will be appreciated --.

In Column 8, Line 4: Please delete "independently be OH, $N(R^4)_2$ or" and replace with -- independently be OH, $N(R^3)_2$ or --.

In Column 8, Line 5: Please delete "which $R^4$ is as defined" and replace with -- which $R^3$ is H or $C_{1-6}$alkyl is as defined --.

In Column 29, Compound 5: Please delete the broken bond line connecting the elements N and N and replace with a continuous bond line.

In Column 29, Compound 3: Please delete the broken bond line connecting the elements N and N and replace with a continuous bond line.

In Column 33 (in the top half of the chemical structure): Please delete the broken bond line connecting the elements N and N and replace with a continuous bond line.

In Column 33 (in the bottom half of the chemical structure): Please delete the broke bond line connecting the elements N and N and replace with a continuous bond line.

In Column 35 (in the bottom half of the chemical structure): Please delete the broken bond line connecting the elements N and N and replace with a continuous bond line.

In Column 42, Line 38: Please insert -- Intermediate (13) --.

In Column 43, Line 1: Please delete "Intermediate (13)".

In Column 44, Line 5: Please delete "Intermediate (15)".

In Column 45, Line 61: Please delete "phenyl}yl}carbonyl)" and replace with -- phenyl}carbonyl) --.

In Column 46 (in the bottom half of the chemical structure): Please delete the broken bond line connecting the elements N and N and replace with a continuous bond line.

UNITED STATES PATENT AND TRADEMARK OFFICE
CERTIFICATE OF CORRECTION

PATENT NO. : 7,205,333 B2
APPLICATION NO. : 10/363988
DATED : April 17, 2007
INVENTOR(S) : Wen-Yang Wu et al.

It is certified that error appears in the above-identified patent and that said Letters Patent is hereby corrected as shown below:

IN THE CLAIMS

In Column 63, Claim 10, Formula (B): Please delete "⌒⌒⌒⌒⌒⌒⌒" and replace with -- ^^^^^ --.

Signed and Sealed this

Twenty-fifth Day of November, 2008

JON W. DUDAS
*Director of the United States Patent and Trademark Office*